(12) United States Patent
Gavardinas et al.

(10) Patent No.: US 7,968,587 B2
(45) Date of Patent: Jun. 28, 2011

(54) TETRAHYDROCYCLOPENTA[B]INDOLE COMPOUNDS AS ANDROGEN RECEPTOR MODULATORS

(75) Inventors: Konstantinos Gavardinas, Monrovia, IN (US); Jonathan Edward Green, Avon, IN (US); Prabhakar Kondaji Jadhav, Zionsville, IN (US); Donald Paul Matthews, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 18 days.

(21) Appl. No.: 12/447,693

(22) PCT Filed: Nov. 6, 2007

(86) PCT No.: PCT/US2007/083745
§ 371 (c)(1), (2), (4) Date: Apr. 29, 2009

(87) PCT Pub. No.: WO2008/063867
PCT Pub. Date: May 29, 2008

(65) Prior Publication Data
US 2010/0069404 A1     Mar. 18, 2010

Related U.S. Application Data

(60) Provisional application No. 60/866,484, filed on Nov. 20, 2006.

(51) Int. Cl.
*A61K 31/403* (2006.01)
*C07D 209/60* (2006.01)

(52) U.S. Cl. .................. 514/411; 548/427

(58) Field of Classification Search .............. 548/427; 514/411
See application file for complete search history.

(56) References Cited

U.S. PATENT DOCUMENTS

| | | | |
|---|---|---|---|
| 4,988,820 A | 1/1991 | Boshagen et al. | |
| 5,204,374 A | 4/1993 | Muller et al. | |
| 5,223,517 A | 6/1993 | Muller et al. | |
| 5,272,161 A | 12/1993 | Niewohner et al. | |
| 5,374,647 A | 12/1994 | Bohagen et al. | |
| 7,122,570 B2 | 10/2006 | Koppitz et al. | |
| 2005/0171143 A1 | 8/2005 | Tanimoto et al. | |
| 2006/0074124 A1 | 4/2006 | Napper et al. | |

FOREIGN PATENT DOCUMENTS

| | | |
|---|---|---|
| WO | WO 03/014082 | 2/2003 |
| WO | WO 2005/056527 | 6/2005 |
| WO | WO 2005/092854 | 10/2005 |
| WO | WO 2006/065480 | 6/2006 |
| WO | WO 2006/089053 | 8/2006 |
| WO | WO-2006/089053 A2 * | 8/2006 |
| WO | WO 2007/002181 | 1/2007 |
| WO | 2007047604 | 4/2007 |
| WO | 2008019825 | 2/2008 |
| WO | 2009140448 | 11/2009 |

OTHER PUBLICATIONS

Brown, "Nonsteroidal Selective Androgen Receptors Modulators (SARMs): Designer Androgens with Flexible Structures Provide Clinical Promise," *Endocrinology*, vol. 145, No. 12, pp. 5417-5419 (2004).
Cadilla, et al., "Selective Androgen Receptor Modulators in Drug Discovery: Medicinal Chemistry and Therapeutic Potential," *Current Topics in Medicinal Chemistry*, vol. 6, pp. 245-270 (2006).
Segal, et al., "Therapeutic potential of the SARMs: revisitng the androgen receptor for drug discovery," *Expert Opinion and Investigational Drugs*, vol. 15, No. 4, pp. 377-387 (2006).
Golob, et al., "Antiestrogenic Activities of 3,8-dihydroxy-6,11-dihydrobenzo[a]carbazoles with Sulfur Containing Side chains", *Arch. Pharm. Pharm. Med. Chem.*, vol. 333, No. 9, pp. 305-311 (2000).
International Search Report for PCT/US2007/083745.
Written Opinion of PCT/US2007/083745.
Demand of PCT/US2007/083745.
Reply to Written Opinion of PCT/US2007/038745.
IPRP for PCT/US2007/038745.
Rejection for U.S. Appl. No. 11/917,398.
U.S. Appl. No. 12/943,163.
Filing Receipt for U.S. Appl. No. 12/943,163.

* cited by examiner

*Primary Examiner* — Joseph K. McKane
*Assistant Examiner* — Janet L Coppins
(74) *Attorney, Agent, or Firm* — Francis O. Ginah; Alexander Wilson

(57) ABSTRACT

The present invention provides a compound of the formula: Formula (I) or a pharmaceutically acceptable salt thereof; pharmaceutical compositions comprising a compound of Formula (I) in combination with a suitable carrier, diluent, or excipient; and methods for treating physiological disorders, particularly reduced bones mass, osteoporosis, osteopenia, or reduced muscle mass or strength, comprising administering a compound of Formula (I), or a pharmaceutically acceptable salt thereof. X-17142.

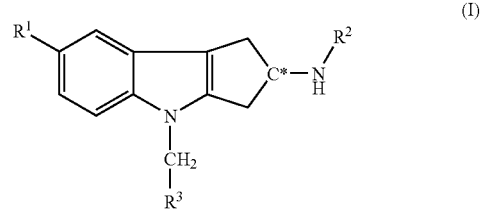

20 Claims, No Drawings

TETRAHYDROCYCLOPENTA[B]INDOLE COMPOUNDS AS ANDROGEN RECEPTOR MODULATORS

This application is the U.S. National Stage filing of PCT Application Serial No. PCT/US2007/083745, filed 6 Nov. 2007, which claims the benefit of U.S. Provisional Application Ser. No. 60/866,484, filed 20 Nov. 2006, hereby incorporated by reference in its entirety.

TECHNICAL FIELD OF INVENTION

The present invention relates to tetrahydrocyclopent[b]indole compounds, or pharmaceutically acceptable salts thereof, that are useful as therapeutic agents, to pharmaceutical compositions comprising the compounds or salts, to methods of using the compounds or salts to treat disorders in patients, and to intermediates and processes useful in the synthesis of the compounds.

BACKGROUND OF THE INVENTION

Endogenous steroidal androgens exert profound influences on a multitude of physiological functions. The effects of steroidal androgens (e.g. testosterone and 5α-dihydrotestosterone (DHT)) are mediated by the androgen receptor (AR) and may be characterized as anabolic or androgenic in nature. Following androgen binding, the AR undergoes a conformational change then translocates to the cell nucleus where it binds to specific DNA sequences termed androgen response elements (AREs) to initiate or repress transcription of target genes. Anabolic (i.e. tissue building) effects of androgens include increasing muscle mass and strength and bone mass, whereas androgenic (i.e. masculinizing) effects include the development of male secondary sexual characteristics such as the internal reproductive tissues (i.e. prostate and seminal vesicle), the external genetalia (penis and scrotum), libido, and hair growth patterns.

Reductions in androgen levels as may occur with aging are associated with serious effects in both males and females. For example, as men age and testosterone levels decline, bones weaken, diabetes and cardiovascular disease rates increase, and the ratio of muscle mass to fat decreases. In females, low plasma levels of circulating testosterone are associated with diminished libido, unexplained fatigue, general lack of well being, and a loss of bone mineral density in post menopausal women. Clinically, the principal application of androgen therapy has been in the treatment of hypogonadism in men. Significantly, androgen replacement therapy in hypogonadal men has also been shown to decrease bone resorption and increase bone mass. Other indications for which androgens have been used clinically include treatment of delayed puberty in boys, anemia, primary osteoporosis, and muscle wasting diseases. In addition, androgen replacement therapy has been used recently in aging men and for the regulation of male fertility. In females, androgen therapy has been used clinically for the treatment of sexual dysfunction or diminished libido.

However, androgen therapy has limitations. For example, unwanted side effects of steroidal androgen therapy include growth stimulation of the prostate and seminal vesicles. In addition, stimulation of prostate tumors and elevations in prostate specific antigen (PSA) (an indication of increased prostate cancer risk), have been associated with androgen use. Furthermore, preparations of unmodified and modified steroidal androgens have been found to suffer from rapid degradation in the liver leading to poor oral bioavailability and short duration of activity following parenteral administration, variations in plasma levels, hepatotoxicity, or cross reactivity with other steroid hormone receptors (e.g. the glucocorticoid receptor (GR), the mineralocorticoid receptor (MR), and the progesterone receptor (PR)). Furthermore, in females, the use of steroidal androgens may lead to hirsutism or virilization.

Thus, there remains a need in the art for alternatives to steroidal androgen therapy which possess the beneficial pharmacological properties of steroidal androgens, but with a reduced likelihood or incidence of the typical limitations associated with steroidal androgen therapy. Recent efforts to identify suitable replacements for steroidal androgens have focused on identifying tissue selective androgen receptor modulators (SARMs) which display a differentiated profile of activity in androgenic tissues. In particular, such agents preferably display androgen agonist activity in anabolic tissues such as muscle or bone, yet are only partial agonists or even antagonists in other androgenic tissues such as the prostate or seminal vesicles.

Thus, it is an object of the present invention to provide nonsteroidal AR ligands which possess androgen agonist activity. More particularly, it is an object to provide nonsteroidal androgen agonists which bind to AR with greater affinity relative to the other steroid hormone receptors. Even more particularly, it is an object to provide tissue selective androgen receptor modulators (SARMs) which display androgen agonist activity in muscle or bone, but only partial agonist, partial antagonist or antagonist activity in androgenic tissues such as the prostate or seminal vesicle.

The following references provide examples of the current state of the art as it relates to the present invention:

Brown, *Endocrinology* (2004); 145(12): 5417-5419 provides a review of nonsteroidal selective androgen receptor modulators.

Cadilla et al., *Curr. Top. Med. Chem* (2006); 6(3): 245-270 provides a review of androgen receptor modulators.

Segal et al., *Expert Opin. Investig. Drugs* (2006); 15(4); 377-387 provides a review of androgen receptor modulators.

Co-pending International Application PCT/US2006/024122 discloses tetrahydrocarbazole compounds as androgen receptor modulators.

SUMMARY OF THE INVENTION

The present invention is directed to the discovery that certain tetrahydrocyclopenta[b]indole compounds, as defined by Formula (I) below, have particular profiles of activity which suggest they are useful in the treatment of disorders responsive to steroidal androgen therapy. Accordingly, the present invention provides a compound of Formula (I):

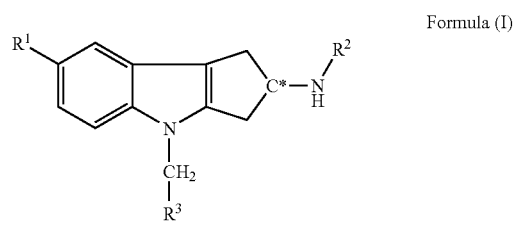

Formula (I)

wherein,
the "C*" carbon center may be in the R, S or R/S configuration;

$R^1$ represents cyano, —CH=NOCH$_3$, —OCHF$_2$, or —OCF$_3$;

$R^2$ represents —COR$^{2a}$ or —SO$_2$R$^{2b}$;

$R^{2a}$ represents (C$_1$-C$_4$)alkyl, (C$_1$-C$_4$)alkoxy, cyclopropyl, or —NR$^a$R$^b$;

$R^{2b}$ represents (C$_1$-C$_4$)alkyl, cyclopropyl, or —NR$^a$R$^b$;

$R^a$ and $R^b$ each independently represent at each occurrence H or (C$_1$-C$_4$)alkyl; and $R^3$ represents a heteroaryl group selected from the group consisting of pyridinyl, pyrimidinyl, pyrazinyl, pyridazinyl, thiazolyl, isothiazolyl, and thiadiazolyl, each of which is optionally substituted with 1 or 2 substituents independently selected from the group consisting of methyl, ethyl, bromo, chloro, fluoro, —CHF$_2$, —CF$_3$, hydroxy, amino, and —NHCH$_2$CO$_2$H, or a pharmaceutically acceptable salt thereof.

In another embodiment, the present invention provides a method of treating hypogonadism, reduced bone mass or density, osteoporosis, osteopenia, reduced muscle mass or strength, sarcopenia, Age Related Functional Decline, delayed puberty in boys, anemia, male or female sexual dysfunction, erectile dysfunction, reduced libido, depression, or lethargy, comprising administering to a patient in need thereof an effective amount of a compound of Formula (I), or a pharmaceutically acceptable salt thereof. As a more particular aspect, the present invention provides a method for treating reduced bone mass or density, osteoporosis, osteopenia, or reduced muscle mass or strength.

Further, the present invention provides the use of a compound of Formula (I), or a pharmaceutically acceptable salt thereof, as an agent for the treatment of hypogonadism, reduced bone mass or density, osteoporosis, osteopenia, reduced muscle mass or strength, sarcopenia, Age Related Functional Decline, delayed puberty in boys, anemia, male or female sexual dysfunction, erectile dysfunction, reduced libido, depression, or lethargy. More particularly, the invention provides the use of a compound of Formula (I), or a pharmaceutically acceptable salt thereof, as an agent for the treatment of reduced bone mass or density, osteoporosis, osteopenia, or reduced muscle mass or strength. In addition, the present invention provides a compound of Formula (I), or a pharmaceutically acceptable salt thereof, for use in therapy.

In another embodiment, the present invention provides the use of a compound of Formula (I), or a pharmaceutically acceptable salt thereof for the manufacture of a medicament for the treatment of hypogonadism, reduced bone mass or density, osteoporosis, osteopenia, reduced muscle mass or strength, sarcopenia, Age Related Functional Decline, delayed puberty in boys, anemia, male or female sexual dysfunction, erectile dysfunction, reduced libido, depression, or lethargy. More particularly, the present invention provides the use of a compound of Formula (I) for the manufacture of a medicament for the treatment of reduced bone mass or density, osteoporosis, osteopenia, or reduced muscle mass or strength.

In addition, the present invention provides a pharmaceutical composition comprising a compound of Formula (I), or a pharmaceutically acceptable salt thereof, in combination with one of more pharmaceutically acceptable carriers, diluents, or excipients. More particularly, the present invention provides a pharmaceutical composition for the treatment of reduced bone mass or density, osteoporosis, osteopenia, or reduced muscle mass or strength, comprising a compound of Formula (I), or a pharmaceutically acceptable salt thereof, in combination with one of more pharmaceutically acceptable carriers, diluents or excipients.

The present invention also encompasses novel intermediates and processes useful for the synthesis of a compound of Formula (I).

DETAILED DESCRIPTION OF THE INVENTION

The present invention relates to novel tetrahydro-cyclopentaindole compounds, as given by Formula (I) herein. As evidenced by in vitro and in vivo testing, exemplified compounds of Formula (I) possess profiles of activity which suggest they have utility in the treatment of disorders responsive to steroidal androgen therapy. In particular, exemplified compounds of Formula (I) are potent AR ligands which agonize the androgen receptor. In addition, exemplified compounds of Formula (I) selectively bind to AR relative to each of MR, GR, and PR.

The compound of Formula (I), or a pharmaceutically acceptable salt thereof, is believed to be useful in the treatment of disorders typically treated with androgen therapy. Thus, methods for the treatment of disorders responsive to androgen therapy constitute and important embodiment of the present invention. Such disorders include hypogonadism, reduced bone mass or density, osteoporosis, osteopenia, reduced muscle mass or strength, sarcopenia, Age Related Functional Decline, delayed puberty in boys, anemia, male or female sexual dysfunction, erectile dysfunction, reduced libido, depression, and lethargy. More particular disorders for which the compounds of Formula (I) are believed to useful include reduced bone mass or density, osteoporosis, osteopenia, or reduced muscle mass or strength.

The present invention also relates to solvates of the compound of Formula (I) or pharmaceutically acceptable salts of compounds of Formula (I). As such, when used herein the term "Formula (I)", or any particular compound of Formula (I), includes within its meaning any pharmaceutically acceptable salt and any solvate of the compound or pharmaceutically acceptable salt thereof. Examples of pharmaceutically acceptable salts and methods for their preparation are well within the knowledge of those skilled in the art. See for example, Stahl et al., "Handbook of Pharmaceutical Salts: Properties, Selection and Use," VCHA/Wiley-VCH, (2002); Gould, P. L., "Salt selection for basic drugs," *International Journal of Pharmaceutics*, 33: 201-217 (1986); Berge et al., "Pharmaceutical Salts," *Journal of Pharmaceutical Sciences*, 66, No. 1, (January 1977); and Bastin et al. "Salt Selection and Optimization Procedures for Pharmaceutical New Chemical Entities," *Organic Process Research and Development*, 4: 427-435 (2000).

The compounds of the present invention have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. Except as set forth herein, all such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981, as well as those techniques provided in the Schemes and Examples herein.

The terms "R" and "S" are used herein as commonly used in organic chemistry to denote specific configurations of a chiral center. The terms "(±)" or "RS" refer to a configuration of a chiral center comprising a racemate. A partial list of priorities and a discussion of stereochemistry is contained in "Nomenclature of Organic Compounds: Principles and Practice", (J. H. Fletcher, et al., eds., 1974).

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As used herein the term "$(C_1-C_4)$alkyl" refers to a straight or branched, monovalent, saturated aliphatic chain of 1 to 4 carbon atoms.

As used herein, the term "$(C_1-C_4)$alkoxy" refers to an oxygen atom bearing a straight or branched, monovalent, saturated aliphatic chain of 1 to 4 carbon atoms.

As used herein, the terms "halo", "halide", or "Hal" refer to a chlorine, bromine, iodine or fluorine atom, unless otherwise specified herein.

As will be appreciated by one of ordinary skill in the art, some of the heteroaryl moieties of the compounds of Formula (I) may exist as positional isomers and as tautomeric forms. The present invention contemplates all positional isomers, individual tautomeric forms, as well as any combination thereof in the names of the heteroaryl moieties of the compounds of Formula I.

The designation "▬◀" refers to a bond that protrudes forward out of the plane of the page.

The designation "⋯⋯" refers to a bond that protrudes backward out of the plane of the page.

The designation "∿∿" refers to a bond that exists as a mixture of bonds that protrude both forward and backward out of the plane of the page.

As appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of disorders contemplates both acute events and chronic conditions. In an acute event, compound is administered at the onset of symptoms and discontinued when the symptoms disappear. As described above, a chronic condition is treated throughout the course of the disease.

As used herein the term "patient" refers to a human or nonhuman mammal such as a dog, cat, cow, monkey, horse, pig, or sheep. It is understood, however, that a particular patient to which a compound of Formula (I), or a pharmaceutically acceptable salt thereof, may be administered is a human.

The term "treating" (or "treat" or "treatment") as used herein includes prohibiting, preventing, restraining, slowing, stopping, or reversing the progression or severity of a symptom or disorder. As such, the methods of this invention encompass both therapeutic and prophylactic use.

Compounds of the present invention may be formulated as part of a pharmaceutical composition. As such, a pharmaceutical composition comprising a compound of Formula (I), or a pharmaceutically acceptable salt thereof, in combination with a pharmaceutically acceptable carrier, diluent or excipient is an important embodiment of the invention. Examples of pharmaceutical compositions and methods for their preparation are well known in the art. See, e.g. REMINGTON: THE SCIENCE AND PRACTICE OF PHARMACY (A. Gennaro, et al., eds., 19$^{th}$ ed., Mack Publishing (1995)). Illustrative compositions comprising compounds of Formula (I) include, for example: A compound of Formula (I) in suspension with 1% sodium carboxymethyl cellulose, 0.25% polysorbate 80, and 0.05% Antifoam 1510™ (Dow Corning); and a compound of Formula (I) in suspension with 0.5% methylcellulose, 0.5% sodium lauryl sulfate, and 0.1% Antifoam 1510 in 0.01N HCl (final pH about 2.5-3) A preferred composition of the present invention comprises a compound of Formula (I), or a pharmaceutically acceptable salt thereof, formulated in a capsule or tablet. A compound of Formula (I), or a composition comprising a compound of Formula (I) can be administered by any route which makes the compound bioavailable, including oral and parenteral routes.

One of skill in the art will appreciate that particle size can affect the in vivo dissolution of a pharmaceutical agent which, in turn, can affect absorption of the agent. "Particle size" as used herein, refers to the diameter of a particle of a pharmaceutical agent as determined by conventional techniques such as laser light scattering, laser diffraction, Mie scattering, sedimentation field flow fractionation, photon correlation spectroscopy, and the like. Where pharmaceutical agents have poor solubility, small or reduced particle sizes may help dissolution and, thus, increase absorption of the agent. Amidon et al., *Pharm. Research*, 12; 413-420 (1995). Methods for reducing or controlling particle size are conventional and include milling, wet grinding, micronization, and the like. Another method for controlling particle size involves preparing the pharmaceutical agent in a nanosuspension. A particular embodiment of the present invention comprises a compound of Formula (I), or a pharmaceutical composition comprising a compound of Formula (I), wherein said compound has an average particle size less than about 20 µm or a d90 particle size (i.e. the maximal size of 90% of the particles) of less than about 50 µm. A more particular embodiment comprises a compound of Formula I having an average particle size less than about 10 µm or a d90 particle size of less than about 30 µm.

As used herein the term "effective amount" refers to the amount or dose of a compound of Formula (I) which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular compound administered; the mode of administration; the bioavailability characteristics of the preparation administered; the dose regimen selected; and the use of any concomitant medications.

When used in conjunction with the methods and uses of the present invention, the compounds and compositions of the present invention may be administered either alone, or in combination with conventional therapeutic agents used to treat the particular disorder or condition. Where the compounds or compositions of the present invention are used as part of a combination, the compound or composition comprising Formula (I) may be administered separately or as part of a formulation comprising the therapeutic agent with which it is to be combined.

Combination Therapy for Bone Loss, Osteoporosis, or Osteopenia:

Conventional therapeutic agents for the treatment of osteoporosis may advantageously be combined with the compounds of Formula (I), or compositions comprising a compound of Formula (I). Conventional agents for the treatment of osteoporosis include hormone replacement therapies such as conjugated equine estrogen (Premarin™), synthetic conjugated estrogen (Cenestin™), esterified estrogen (Estratab™ or Menest™), estropiate (Ogen™ or Ortho-est™); as well as transdermal estradiol preparations such as Alora™, Climara™, Estraderm™, and Vivelle™. Combination estrogen-progestin formulations are also available for the treatment of osteoporosis including Prempro™ (conjugated equine estrogen and medroxyprogesterone acetate), Premphase™ (conjugated equine estrogen and norgestimate), Ortho-Prefest™ (estradiol and norgestimate), Femhrt™ (ethinyl estradiol and norethindrone acetate), and Combipatch™ (transdermal estradiol and norethindrone acetate). Other conventional osteoporosis treatments which may be combined with the compounds or compositions of the present invention include bisphosphonates such as alendronate (Fosamax™) risedronate (Actonel™), and pamidronate (Aredia™); selective estrogen receptor modulators (SERMs) such as raloxifene (Evista™); calcitonin (Calcimar™ or Miacalcin™); parathyroid hormone (Forteo™); calcium; Vitamin D; diuretics (to reduce $Ca^{2+}$ excretion); fluoride; and androgens (e.g. testosterone or 5α-dihydrotestosterone).

Thus, a formulation for combination therapy in treating osteoporosis comprises:

Ingredient (A1): a compound of Formula (I);

Ingredient (A2): one or more co-agents that are conventional for the treatment of osteoporosis selected from the group consisting of Premarin™, Cenestin™, Estratab™, Menest™, Ogen™, Ortho-est™, Alora™, Climara™, Estraderm™, Vivelle™, Prempro™, Premphase™, Ortho-Prefest™, Femhrt™, Combipatch™, Fosamax™), Actonel™, Aredia™); Evista™; Calcimar™, Miacalcin™, Forteo™, calcium, Vitamin D, diuretics, fluoride, testosterone, and 5α-dihydrotestosterone; and optionally Ingredient (A3): a pharmaceutically acceptable carrier, diluent or excipient.

Particular Aspects of the Invention

The following list sets out several groupings of particular substituents and particular variables for compounds of Formula (I). It will be understood that compounds of Formula (I) having such particular substituents or variables, as well as methods and uses employing such compounds, represent particular aspects of the present invention.

Thus, a particular aspect of the present invention is one wherein the compound of Formula (I) is one wherein $R^2$ and $R^3$ have any of the values defined herein, and:

(a) $R^1$ represents cyano, —CH=NOCH$_3$, or —OCF$_3$; or
(b) $R^1$ represents cyano or —CH=NOCH$_3$; or
(c) $R^1$ represents cyano; or
(d) $R^1$ represents —CH=NOCH$_3$.

Additional particular aspects of the present invention are those wherein the compound of Formula (I) is one wherein $R^1$ and $R^3$ have any of the values defined herein, and:

(a) $R^2$ represents —COR$^{2a}$ or —SO$_2$R$^{2b}$ wherein $R^{2a}$ represents (C$_1$-C$_4$)alkyl, (C$_1$-C$_4$)alkoxy, cyclopropyl, or —N(CH$_3$)$_2$ and $R^{2b}$ represents (C$_1$-C$_4$)alkyl, cyclopropyl, —N(CH$_3$)$_2$ or —N(C$_2$H$_5$)$_2$; or (b) $R^2$ represents —COR$^{2a}$ or —SO$_2$R$^{2b}$ wherein $R^{2a}$ represents ethyl, isopropyl, methoxy, ethoxy, propoxy, isopropoxy, isobutoxy, tert-butoxy, cyclopropyl, or —N(CH$_3$)$_2$ and $R^{2b}$ represents methyl, ethyl, propyl, cyclopropyl, —N(CH$_3$)$_2$ or —N(C$_2$H$_5$)$_2$; or (c) $R^2$ represents —COR$^{2a}$, wherein $R^{2a}$ represents ethyl, isopropyl, methoxy, ethoxy, propoxy, isopropoxy, isobutoxy, tert-butoxy, cyclopropyl, or —N(CH$_3$)$_2$; or (d) $R^2$ represents —COR$^{2a}$, wherein $R^{2a}$ represents isopropyl, ethoxy, isopropoxy, or cyclopropyl; or (e) $R^2$ represents —COR$^{2a}$, wherein $R^{2a}$ represents isopropoxy; or (f) $R^2$ represents —SO$_2$R$^{2b}$, wherein $R^{2b}$ represents methyl, ethyl, propyl, cyclopropyl, —N(CH$_3$)$_2$ or —N(C$_2$H$_5$)$_2$; or (g) $R^2$ represents —SO$_2$R$^{2b}$, wherein $R^{2b}$ represents cyclopropyl or —N(CH$_3$)$_2$; or (h) $R^2$ represents —SO$_2$R$^{2b}$, wherein $R^{2b}$ represents —N(CH$_3$)$_2$.

Additional particular aspects of the present invention are those wherein the compound of Formula (I) is one wherein $R^1$ and $R^2$ have any of the values defined herein, and:

(a) $R^2$ represents —COR$^{2a}$ and the "C*" carbon center is in the S configuration; or (b) $R^2$ represents —SO$_2$R$^{2b}$ and the "C*" carbon center is in the R configuration Additional particular aspects of the present invention are those wherein the compound of Formula (I) is one wherein $R^1$ and $R^2$ have any of the values defined herein, and:

(a) $R^3$ represents a heteroaryl group selected from the group consisting of pyridinyl, pyrimidinyl, pyrazinyl, pyridazinyl, thiazolyl, isothiazolyl, and thiadiazolyl, each of which is optionally substituted with 1 or 2 substituents independently selected from the group consisting of methyl, bromo, chloro, fluoro, —CHF$_2$, hydroxy, amino, and —NHCH$_2$CO$_2$H; or (b) $R^3$ represents 6-fluoro-pyridin-2-yl, pyridin-2-yl, 3-hydroxy-pyridin-2-yl, 6-difluoromethyl-pyridin-2-yl, 2-amino-pyridin-3-yl, 2-carboxymethylamino-pyridin-3-yl, pyrimidin-4-yl, pyrimidin-2-yl, 2-chloro-pyrimidin-4-yl, thiazol-4-yl, 2-methyl-thiazol-4-yl, 2-chloro-thiazol-4-yl, thiazol-2-yl, thiazol-5-yl, 4-Amino-thiazol-5-yl, pyrazin-2-yl, 5-methyl-pyrazin-2-yl, 3-chloro-pyrazin-2-yl, 6-methyl-pyrazin-2-yl, 3-amino-pyrazin-2-yl, 3-methyl-pyrazin-2-yl, pyridazin-3-yl, 5-bromo-isothiazol-3-yl, isothiazol-3-yl, 4,5-dichloro-isothiazol-3-yl, or [1,2,5]thiadiazol-3-yl;

(c) $R^3$ represents 6-fluoro-pyridin-2-yl, pyridin-2-yl, 3-hydroxy-pyridin-2-yl, 6-difluoromethyl-pyridin-2-yl, 2-amino-pyridin-3-yl, 2-carboxymethylamino-pyridin-3-yl, thiazol-4-yl, 2-methyl-thiazol-4-yl, 2-chloro-thiazol-4-yl, thiazol-2-yl, thiazol-5-yl, 4-amino-thiazol-5-yl, pyrazin-2-yl, 5-methyl-pyrazin-2-yl, 3-chloro-pyrazin-2-yl, 6-methyl-pyrazin-2-yl, 3-amino-pyrazin-2-yl, or 3-methyl-pyrazin-2-yl;

(d) $R^3$ represents 6-fluoro-pyridin-2-yl, pyridin-2-yl, 2-amino-pyridin-3-yl, thiazol-5-yl, or 4-amino-thiazol-5-yl; or (e) $R^3$ represents pyridin-2-yl, 2-amino-pyridin-3-yl, thiazol-5-yl, or 4-amino-thiazol-5-yl.

A more particular aspect of the present invention is one wherein the compound of Formula (I), is one wherein, the "C*" carbon center is in the S configuration when $R^2$ represents —COR$^{2a}$ and in the R configuration when $R^2$ represents —SO$_2$R$^{2b}$;

$R^1$ represents cyano or —CH=NOCH$_3$;

$R^2$ represents —COR$^{2a}$ or —SO$_2$R$^{2b}$ wherein R$^{2a}$ represents (C$_1$-C$_4$)alkyl, (C$_1$-C$_4$)alkoxy, cyclopropyl, or —N(CH$_3$)$_2$ and R$^{2b}$ represents (C$_1$-C$_4$)alkyl, cyclopropyl, —N(CH$_3$)$_2$ or —N(C$_2$H$_5$)$_2$; and $R^3$ represents a heteroaryl group selected from the group consisting of pyridinyl, pyrimidinyl, pyrazinyl, pyridazinyl, thiazolyl, isothiazolyl, and thiadiazolyl, each of which is optionally substituted with 1 or 2 substituents independently selected from the group consisting of methyl, bromo, chloro, fluoro, —CHF$_2$, hydroxy, amino, and —NHCH$_2$CO$_2$H;

An even more particular aspect of the present invention is one wherein the compound of Formula (I), is one wherein, the "C*" carbon center is in the S configuration when R$^2$ represents —COR$^{2a}$ and in the R configuration when R$^2$ represents —SO$_2$R$^{2b}$;

$R^1$ represents cyano or —CH=NOCH$_3$;

$R^2$ represents —COR$^{2a}$ or —SO$_2$R$^{2b}$ wherein R$^{2a}$ represents ethyl, isopropyl, methoxy, ethoxy, propoxy, isopropoxy, isobutoxy, tert-butoxy, cyclopropyl, or —N(CH$_3$)$_2$ and R$^{2b}$ represents methyl, ethyl, propyl, cyclopropyl, —N(CH$_3$)$_2$ or —N(C$_2$H$_5$)$_2$; and $R^3$ represents 6-fluoro-pyridin-2-yl, pyridin-2-yl, 3-hydroxy-pyridin-2-yl, 6-difluoromethyl-pyridin-2-yl, 2-amino-pyridin-3-yl, 2-carboxymethylamino-pyridin-3-yl, pyrimidin-4-yl, pyrimidin-2-yl, 2-chloro-pyrimidin-4-yl, thiazol-4-yl, 2-methyl-thiazol-4-yl, 2-chloro-thiazol-4-yl, thiazol-2-yl, thiazol-5-yl, 4-amino-thiazol-5-yl, pyrazin-2-yl, 5-methyl-pyrazin-2-yl, 3-chloro-pyrazin-2-yl, 6-methyl-pyrazin-2-yl, 3-amino-pyrazin-2-yl, 3-methyl-pyrazin-2-yl, pyridazin-3-yl, 5-bromo-isothiazol-3-yl, isothiazol-3-yl, 4,5-dichloro-isothiazol-3-yl, or [1,2,5]thiadiazol-3-yl;

An even more particular aspect of the present invention is one wherein the compound of Formula (I), is one wherein, the "C*" carbon center is in the S configuration when R$^2$ represents —COR$^{2a}$ and in the R configuration when R$^2$ represents —SO$_2$R$^{2b}$;

$R^1$ represents cyano;

$R^2$ represents —COR$^{2a}$ or —SO$_2$R$^{2b}$ wherein R$^{2a}$ represents isopropyl, ethoxy, isopropoxy, or cyclopropyl; and R$^{2b}$ represents cyclopropyl or —N(CH$_3$)$_2$; and $R^3$ represents 6-fluoro-pyridin-2-yl, pyridin-2-yl, 2-amino-pyridin-3-yl, thiazol-5-yl, or 4-amino-thiazol-5-yl.

An even more particular aspect of the present invention is one wherein the compound of Formula (I), is one wherein, the "C*" carbon center is in the S configuration when R$^2$ represents —COR$^{2a}$ and in the R configuration when R$^2$ represents —SO$_2$R$^{2b}$;

$R^1$ represents cyano;

$R^2$ represents —COR$^{2a}$ or —SO$_2$R$^{2b}$ wherein R$^{2a}$ represents isopropoxy and R$^{2b}$ represents —N(CH$_3$)$_2$; and $R^3$ represents pyridin-2-yl, 2-amino-pyridin-3-yl, thiazol-5-yl, or 4-amino-thiazol-5-yl.

Additional particular aspects of the present invention are provided by the compounds of Formula I(a) and Formula I(b) below. It will be understood that compounds of Formula I(a) and Formula I(b), as well as methods and uses employing such compounds, represent particular further aspects of the present invention.

Thus, a particular aspect of the present invention is provided by Formula I(a)

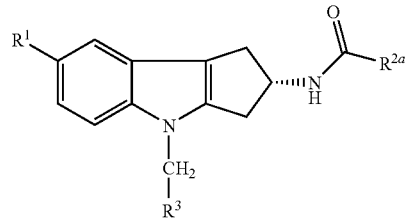

Formula I(a)

wherein, $R^1$ represents cyano, —CH=NOCH$_3$, or —OCF$_3$;

$R^{2a}$ represents (C$_1$-C$_4$)alkyl, (C$_1$-C$_4$)alkoxy, cyclopropyl, or —N(CH$_3$)$_2$; and $R^3$ represents a heteroaryl group selected from the group consisting of pyridinyl, pyrimidinyl, pyrazinyl, pyridazinyl, thiazolyl, isothiazolyl, and thiadiazolyl, each of which is optionally substituted with 1 or 2 substituents independently selected from the group consisting of methyl, bromo, chloro, fluoro, —CHF$_2$, hydroxy, amino, and —NHCH$_2$CO$_2$H.

Even more particular is a compound of Formula I(a), wherein $R^1$ represents cyano or —CH=NOCH$_3$;

$R^{2a}$ represents ethyl, isopropyl, methoxy, ethoxy, propoxy, isopropoxy, isobutoxy, tert-butoxy, cyclopropyl, or —N(CH$_3$)$_2$; and $R^3$ represents 6-fluoro-pyridin-2-yl, pyridin-2-yl, 3-hydroxy-pyridin-2-yl, 6-difluoromethyl-pyridin-2-yl, 2-amino-pyridin-3-yl, 2-carboxymethylamino-pyridin-3-yl, pyrimidin-4-yl, pyrimidin-2-yl, 2-chloro-pyrimidin-4-yl, thiazol-4-yl, 2-methyl-thiazol-4-yl, 2-chloro-thiazol-4-yl, thiazol-2-yl, thiazol-5-yl, 4-amino-thiazol-5-yl, pyrazin-2-yl, 5-methyl-pyrazin-2-yl, 3-chloro-pyrazin-2-yl, 6-methyl-pyrazin-2-yl, 3-amino-pyrazin-2-yl, 3-methyl-pyrazin-2-yl, pyridazin-3-yl, 5-bromo-isothiazol-3-yl, isothiazol-3-yl, 4,5-dichloro-isothiazol-3-yl, or [1,2,5]thiadiazol-3-yl.

A further particular aspect is provided by Formula I(a), wherein $R^1$ represents cyano;

$R^{2a}$ represents isopropyl, isopropoxy, ethoxy, or cyclopropyl; and $R^3$ represents 6-fluoro-pyridin-2-yl, pyridin-2-yl, 2-amino-pyridin-3-yl, thiazol-5-yl, or 4-amino-thiazol-5-yl.

As stated, another particular aspect of the present invention is provided by Formula I(b)

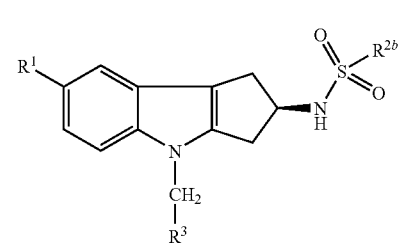

Formula I(b)

wherein, $R^1$ represents cyano or —CH=NOCH$_3$;

$R^{2b}$ represents (C$_1$-C$_4$)alkyl, cyclopropyl, —N(CH$_3$)$_2$ or —N(C$_2$H$_5$)$_2$; and $R^3$ represents a heteroaryl group selected from the group consisting of pyridinyl, pyrimidinyl, pyrazinyl, pyridazinyl, thiazolyl, isothiazolyl, and thiadiazolyl, each of which is optionally substituted with 1 or 2 substituents independently selected from the group consisting of methyl, bromo, chloro, fluoro, —CHF$_2$, hydroxy, amino, and —NHCH$_2$CO$_2$H.

Even more particular is a compound of Formula I(b), wherein

R$^1$ represents cyano or —CH=NOCH$_3$;

R$^{2b}$ represents methyl, ethyl, propyl, cyclopropyl, —N(CH$_3$)$_2$ or —N(C$_2$H$_5$)$_2$; and R$^3$ represents isothiazol-3-yl, 6-fluoro-pyridin-2-yl, pyridin-2-yl, 2-amino-pyridin-3-yl, pyrazin-2-yl, thiazol-4-yl, thiazol-2-yl, thiazol-5-yl, 4-amino-thiazol-5-yl, or [1,2,5] thiadiazol-3-yl.

A further particular aspect is provided by Formula I(b), wherein

R$^1$ represents cyano;

R$^{2b}$ represents cyclopropyl or —N(CH$_3$)$_2$; and

R3 represents thiazol-4-yl, thiazol-2-yl, thiazol-5-yl, or 4-amino-thiazol-5-yl.

In addition, it will be understood a most particular aspect of the present invention is provided by those compounds of Formula (I) exemplified herein, most particularly the compound (S)-(7-cyano-4-pyridin-2-ylmethyl-1,2,3,4-tetrahydro-cyclopenta[b]indol-2-yl)-carbamic acid isopropyl ester; (S)-(7-cyano-4-thiazol-5-ylmethyl-1,2,3,4-tetrahydro-cyclopenta[b]indol-2-yl)-carbamic acid isopropyl ester; (S)-[4-(2-amino-pyridin-3-ylmethyl)-7-cyano-1,2,3,4-tetrahydro-cyclopenta[b]indol-2-yl]-carbamic acid isopropyl ester; (R)—N'-[4-(4-amino-thiazol-5-ylmethyl)-7-cyano-1,2,3,4-tetrahydro-cyclopenta[b]indol-2-yl]-N,N-dimethylsulfamide; or (S)-[4-(4-amino-thiazol-5-ylmethyl)-7-cyano-1,2,3,4-tetrahydro-cyclopenta[b]indol-2-yl]-carbamic acid isopropyl ester.

Compounds of the present invention can be chemically prepared, for example, by following the synthetic routes set forth in the Schemes, Intermediates, and Examples below. However, the following discussion is not intended to be limiting to the scope of the present invention in any way. For example, the specific synthetic steps for each of the routes described may be combined in different ways, or in conjunction with steps from different schemes, to prepare additional compounds of Formula (I).

The substituents, unless otherwise indicated, are as previously defined. The reagents and starting materials are readily available to one of ordinary skill in the art. Other necessary reagents and starting material may be made by procedures which are selected from standard techniques of organic and heterocyclic chemistry, techniques which are analogous to the syntheses of known structurally similar compounds, and the procedures described in the Examples below, including any novel procedures.

Scheme I

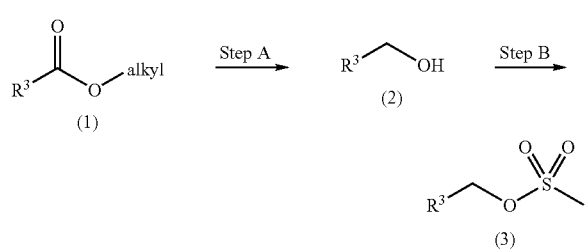

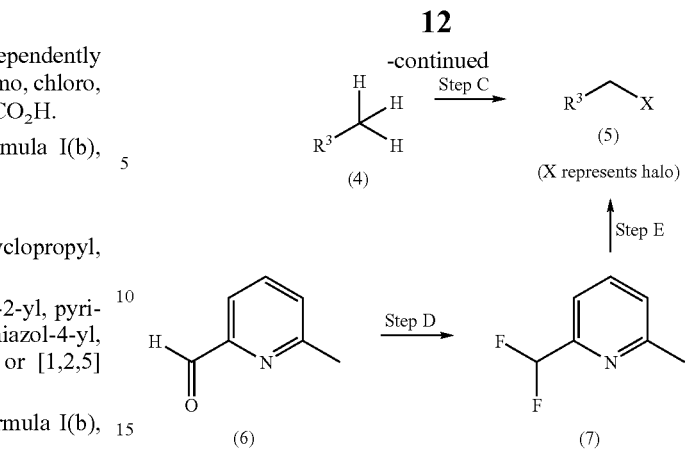

Scheme I describes methods for making R$^3$—CH$_2$—X or R$^3$—CH$_2$—OMs, to be used in subsequent alkylations of tetrahydrocyclopenta[b]indole compounds.

In Scheme I, Step A, the alcohol of formula (2) is obtained by reducing an ester of formula (1). The ester is obtained, if necessary, from the carboxylic acid via the acid chloride using methods well known in the art, such as with oxalyl chloride. Numerous methods for reducing carboxylic esters to alcohols are well known to those skilled in the art and can be found in the text of R. C. Larock in "Comprehensive Organic Transformations", VCH Publishers, 1989, p. 549-551. The preferred method is reduction with lithium borohydride in an aprotic solvent such as tetrahydrofuran at room temperature to reflux temperature for about 1 to 48 hours.

In Scheme I, Step B, an alcohol of formula (2) is converted to a methanesulfonic acid ester of formula (3). The alcohol is combined with an organic base such as triethylamine or diisopropylethylamine and treated with methanesulfonylchloride in an inert solvent such as dichloromethane. The reaction is maintained at 0° C. to room temperature for 15 minutes to 4 hours. The product is isolated by extractive techniques known to one skilled in the art.

In Scheme I, Step C, a compound of formula (4), wherein R$^3$ is heteroaryl, is halogenated to provide an alkyl halide of formula (5). The compound of formula (4) is treated with a free radical initiator such as benzoyl peroxide or 1,1'-azobisisobutyronitrile or 1,1'-azobis(cyclohexanecarbonitrile) in carbon tetrachloride or ethyl acetate with N-chlorosuccinimide or N-bromosuccinimide with or without irradiation from a UV light. The preferred method is treatment with 1,1'-azobis(cyclohexanecarbonitrile) or 1,1'-azobisisobutyronitrile and N-bromosuccinimide at about room temperature to the refluxing temperature of carbon tetrachloride, for about 4 to 48 hours. The product may then be purified using standard techniques such as filtration of insoluble components, followed by silica gel chromatography.

Alternatively in Scheme I, Step C, a heteroarylmethyl of formula (4) can be chlorinated to give an alkyl chloride, wherein X is Cl, using trichloroisocyanuric acid. The reaction is performed in an inert solvent such as chloroform and refluxed for 4 to 72 hours. The product is isolated by filtration through a silica pad, followed by chromatography.

In Scheme I, Step D, a formyl pyridine of formula (6) is converted to a difluoromethylpyridine of formula (7) using bis-(2-methoxyethyl)aminosulfur trifluoride. The reaction is performed in an inert solvent, such as dichloromethane for 4 to 24 hours and then quenched in saturated NaHCO$_3$ solution. The product is then isolated by common extractive techniques.

In Scheme I, Step E, the difluoromethylpyridine of formula (7) is converted to an alkyl bromide of formula (5) (X is Br) as previously described in Scheme I, Step C.

Scheme II

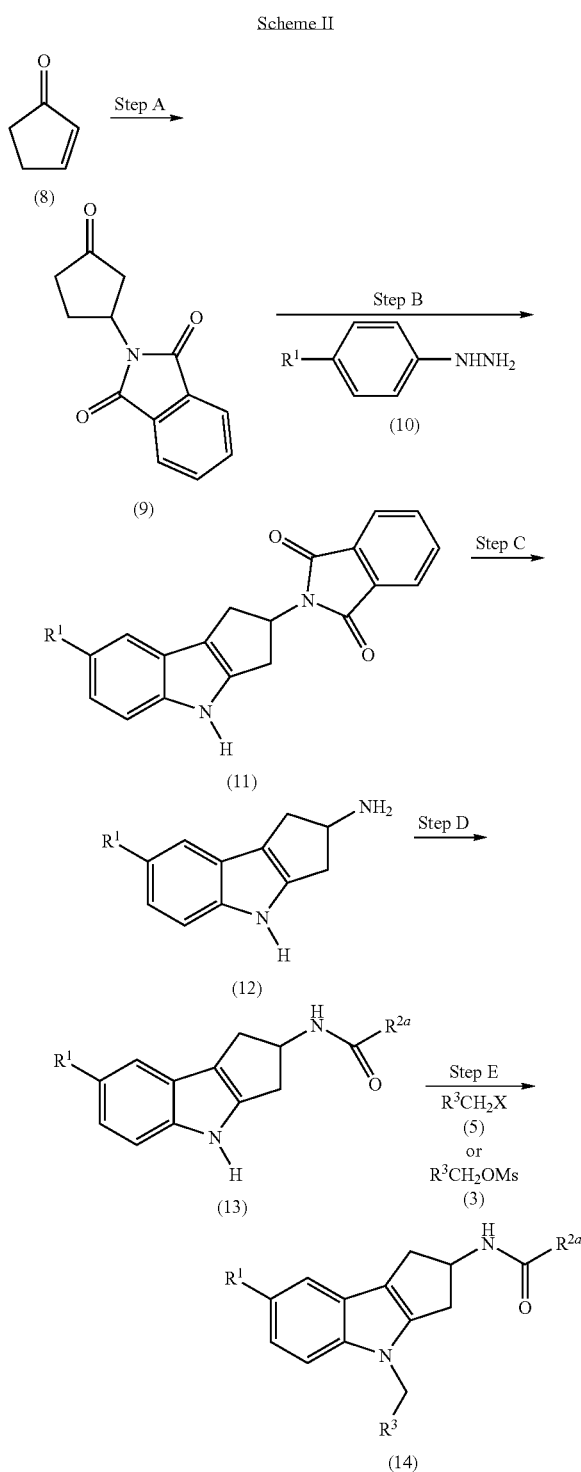

In Scheme II, Step A, cyclopentenone (8) is reacted with phthalimide in a Michael addition to give (±)-2-(3-oxo-cyclopentyl)-isoindole-1,3-dione (9). The reaction is performed in methanol/2N $Na_2CO_3$ in a ratio of 10/1 by volume preferably at ambient temperature using conditions similar to those described by O. Nowitzki, et. al. in *Tetrahedron* 1996, 52, 11799-11810. The product is isolated by addition of water and (9) obtained as a white solid.

In Scheme II, Step B, (±)-2-(3-oxo-cyclopentyl)-isoindole-1,3-dione (9) is reacted with a phenylhydrazine of formula (10) in a typical Fischer indole synthesis to give a tetrahydrocyclopenta[b]indole of formula (11). The skilled artisan will recognize that there are a variety of acidic conditions to effect a Fischer indole synthesis, including both proton and Lewis acids. The preferred conditions use a mixture of glacial acetic acid with 4N HCl in dioxane, at a temperature of 50° C. to the reflux temperature of the solvent, for about 4 to 24 hours. The product is isolated by addition of water followed by filtration of the resulting solid. The solid is sonicated in methanol to give material of sufficient purity. Alternatively, the reaction is effected using a Lewis acid, such as zinc chloride, in an amount of about 2 to 4 equivalents.

Other preferred conditions for Step B use ethanol at reflux temperature for about 4 to 24 hours. The product is isolated and may be purified by filtration of the reaction mixture, followed by silica gel chromatography of the filtrate.

In Scheme II, Step C, the phthalimide group of formula (11) is cleaved with hydrazine or hydrazine hydrate to provide an aminotetrahydrocyclopenta[b]indole of formula (12) using conditions as described by M. Alajarín, et al (*Eur. J. Org. Chem.* 2002, 4222-4227). Preferred conditions use tetrahydrofuran/ethanol in a mixture of about 5.5/1 by volume at a temperature of 0 to 50° C., preferably at about room temperature, for 4 to 72 hours. The resulting phthalhydrazide is removed by filtration and the product isolated by concentration of the filtrate and may be subsequently purified by chromatography using techniques known in the art.

In Scheme II, Step D, an amine of formula (12) is acylated with the appropriate acid chloride, chloroformate, dialkyldicarbonate, or carbamoyl chloride to give an amide, carbamate, or urea of formula (13), wherein $R^2$ is $C(O)R^{2a}$, using conditions well known to those skilled in the art. The amine is combined with an excess of an organic amine base such as triethylamine or diisopropylethylamine in an inert solvent such as tetrahydrofuran, dichloroethane or dichloromethane, N-methylpyrrolidinone, or N,N-dimethylformamide, or a mixture thereof. Preferred conditions use diisopropylethylamine in dichloromethane in the presence, for example, of isopropylchloroformate at a temperature of 0 to 40° C. for 1 to 72 hours. The product is isolated by addition of water and diethyl ether, followed by stirring and collection of the resulting solid. If the product is sufficiently soluble in an appropriate organic solvent, it may be isolated by extractive techniques and then slurried in a suitable organic solvent, such as heptane, and isolated by filtration.

It will be recognized by one skilled in the art that amines such as those of formula (12) are often more suitably stored and handled as an intermediate of formula (13), with the amine suitably protected, such as with a t-butoxycarbonyl (BOC) group, wherein $R^{2a}$ is O-t-butyl, or by formation of an acid addition salt. The BOC group is later removed and the amine acylated to make the desired amide or carbamate of the compounds of the present invention.

In Scheme II, Step E, a tetrahydrocyclopenta[b]indole of formula (13) is alkylated with $R^3CH_2$—X, wherein X is Cl or Br, or $R^3CH_2OSO_2Me$ (see Scheme I), to provide a tetrahydrocyclopenta[b]indole of formula (14). Preferred conditions use $Cs_2CO_3$, in an inert solvent such as DMF, DMSO, or N-methylpyrrolidinone, at a temperature of 20 to 100° C., but preferably at 45 to 60° C., for 2 to 24 hours. The product is isolated by extractive techniques known in the art and purified by silica gel chromatography. Alternatively, the alkylation can be effected using a strong base such as sodium hydride, potassium hydride, potassium bis(trimethylsilyl)amide or sodium bis(trimethylsilyl)amide, in an inert solvent such as dimethylformamide, N-methylpyrrolidinone, or tetrahydrofuran. Preferred conditions use sodium hydride in dimethylformamide at a temperature of 0 to 80° C. for 4 to 48 hours. The alkylated product of formula (14) is isolated by extractive and chromatographic techniques known to those skilled in the art.

Scheme III

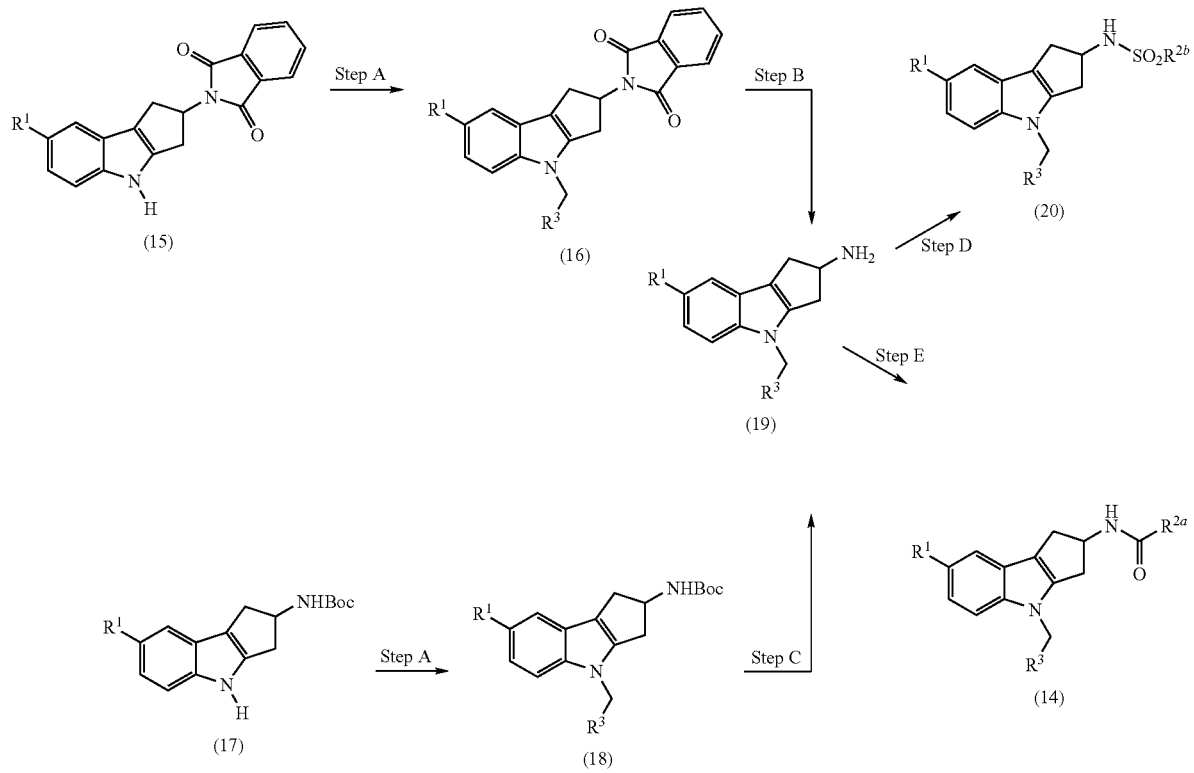

In Scheme III, Step A, a tetrahydrocyclopenta[b]indole of formula (15) or formula (17) is alkylated with R³CH₂X, wherein X is Cl, Br, or with R³CH₂OSO₂Me, as described for Scheme II, Step E, to provide a tetrahydrocyclopentane indole of formula (16) or (18).

In Scheme III, Step B, the phthalimide group of formula (16) is cleaved with hydrazine hydrate or hydrazine to provide an aminotetrahydrocyclopenta[b]indole of formula (19) as described for Scheme II, Step C.

Alternatively, in Scheme III, Step C, an aminotetrahydrocyclopenta[b]indole of formula (19) can be generated from deprotection of the t-butoxycarbonyl (BOC) protected amine of formula (18). Common deprotection conditions for removing a BOC group are well know by those skilled in the art and can be found in the text of T. W. Green and P. G. M. Wuts in "Protective Groups in Organic Synthesis", John Wiley & Sons, Inc., 1991, 328-330. Preferred conditions use 4M hydrogen chloride in dioxane at a temperature of about 0 to 50° C. for about 10 minutes to 24 hours.

In Scheme III, Step D, the amine of formula (19) is converted to a sulfamide or sulfonamide of formula (20) by reaction with the corresponding sulfamoyl or sulfonyl chloride respectively, in an appropriate solvent such as chloroform or dichloromethane at 50-60° C. using a base such as triethylamine, Hunig's base or 1,4-diazabicyclo[2.2.2]-octane (DABCO). Preferred conditions make use of chloroform with DABCO as base.

Alternatively, (14) can be prepared as shown in Scheme III, Step E, by reacting the appropriate acid chloride, chloroformate, or carbamoyl chloride with an amine of formula (19), essentially as described in Scheme II, Step D.

Scheme IV

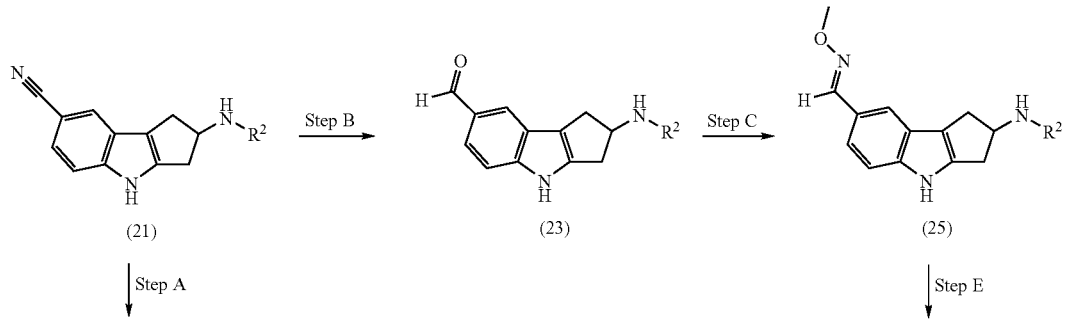

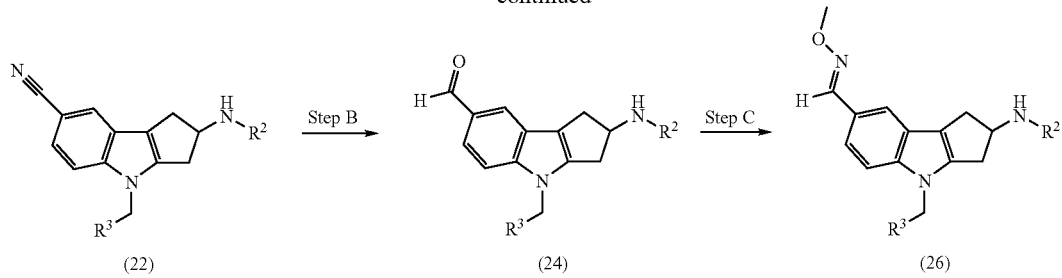

In Scheme IV, Step A, a tetrahydrocyclopenta[b]indole of formula (21) is alkylated as described in Scheme II, Step E to give the substituted tetrahydro-cyclopenta[b]indole of formula (22).

In Scheme IV, Step B, a nitrile of formula (21) or (22), is reduced to an aldehyde of formula (23) or (24). The nitrile is treated with aluminum-nickel catalyst in a solvent mixture of water/formic acid ranging from a ratio of 1/10 to 1/2. The formic acid used can be 98, 96 or 88%. The reaction is performed at room temperature to the reflux temperature of the solvent, for about 2 to 48 hours. The product is isolated by addition of a protic solvent such as methanol, followed by filtration and concentration of the filtrate. The residue is further purified by common extractive techniques such as with sodium bicarbonate solution and ethyl acetate to provide the aldehyde, or by sonication with ethanol, and used without further purification.

Alternatively, in Scheme IV, Step B, when $R^2$ is tert-butoxycarbonyl (BOC), then the nitrile of formula (21) or (22) is reduced using nonacidic conditions, such as with a metal hydride reducing agent, for example with diisobutylaluminum hydride. The reaction is effected in an inert solvent, such as dichloromethane, with addition of diisobutylaluminum hydride, followed by ethyl acetate and stirred for 30 min to 2 hours at room temperature. The reaction is stirred with 20% aqueous sodium tartrate for 1 hour and then isolated using extractive techniques.

In Scheme IV, Step D, an aldehyde of formula (23) or (25) is converted to a methoxime of formula (25) or (26), respectively. The aldehyde is treated with the hydrochloride salt of methoxyamine in ethanol or methanol at 0 to 100° C. for about 2 to 24 hours, preferably at room temperature for one hour, in the presence of a base, such as potassium carbonate, sodium carbonate or sodium hydroxide. The product is isolated by concentrating and triturating the product in water. Alternatively the reaction is diluted with ethyl acetate, isolated using extractive techniques, and may subsequently purified using standard techniques such as chromatography.

In Scheme IV, Step E, a methoxime tetrahydrocyclopentane indole of formula (25) is alkylated to give the N-substituted methoxime tetrahydrocyclopentane indole of formula (26) as described in Scheme II, Step E.

Determination of Biological Activity:

As used herein, "$K_d$" refers to the equilibrium dissociation constant for a ligand-receptor complex; "$K_i$" refers to the equilibrium dissociation constant for drug-receptor complex, and is an indication of concentration of drug that will bind to half the binding sites at equilibrium; "IC50" refers to the concentration of an agent which produces 50% of the maximal inhibitory response possible for that agent or, alternatively, to the concentration of an agent which produces 50% displacement of ligand binding to the receptor; "EC50" refers to the concentration of an agent which produces 50% of the maximal response possible for that agent; and "ED50" refers to the dose of an administered therapeutic agent which produces 50% the maximal response for that agent.

Steroid Hormone Nuclear Receptor Binding Assay:

Cell lysates from human embryonic kidney HEK293 cells overexpressing human GR (glucocorticoid receptor), AR (androgen receptor), MR (mineralocorticoid receptor), or PR (progesterone receptor) are used for receptor-ligand competition binding assays to determine Ki values.

Briefly, steroid receptor competition binding assays are run in a buffer containing 20 mM Hepes buffer (pH=7.6), 0.2 mM EDTA, 75 mM NaCl, 1.5 mM $MgCl_2$, 20% glycerol, 20 mM sodium molybdate, 0.2 mM DTT (dithiothreitol), 20 μg/mL aprotinin and 20 μg/mL leupeptin. Typically, steroid receptor binding assays include radio-labeled ligands, such as 0.3 nM [$^3$H]-dexamethasone for GR binding, 0.36 nM [$^3$H]-methyltrienolone for AR binding, 0.25 nM [$^3$H]-aldosterone for MR binding, and 0.29 nM [$^3$H]-methyltrienolone for PR binding, and either 20 μg 293-GR lysate, 22 μg 293-AR lysate, 20 μg 293-MR lysate or 40 μg 293-PR lysate per well. Assays are typically run in 96-well format. Competing test compounds are added at various concentrations ranging from about 0.01 nM to 10 μM. Non-specific binding is determined in the presence of 500 nM dexamethasone for GR binding, 500 nM aldosterone for MR binding, or 500 nM methyltrienolone for AR and PR binding. The binding reactions (140 μL) are incubated overnight at 4° C., then 70 μL of cold charcoal-dextran buffer (containing per 50 mL of assay buffer, 0.75 g of charcoal and 0.25 g of dextran) is added to each reaction. Plates are mixed for 8 minutes on an orbital shaker at 4° C. The plates are then centrifuged at 3,000 rpm at 4° C. for 10 minutes. An aliquot of 120 μL of the binding reaction mixture is then transferred to another 96-well plate and 175 μL of Wallac Optiphase Hisafe 3™ scintillation fluid is added to each well. Plates are sealed and shaken vigorously on an orbital shaker. After an incubation of 2 hours, plates are read in a Wallac Microbeta counter.

The data are used to calculate an estimated IC50 and percentage inhibition at 10 μM. The Kd for [$^3$H]-dexamethasone for GR binding, [$^3$H]-methyltrienolone for AR binding, [$^3$H]-aldosterone for MR binding, or [$^3$H]-methyltrienolone for PR binding, is determined by saturation binding. The IC50 values for compounds are converted to Ki using the Cheng-Prusoff equation.

Following a protocol essentially as described above, the exemplified compounds of the present invention display a Ki in the AR binding assay of ≦500 nM. Preferably, compounds of the present invention display a Ki in the AR binding assay of ≦100 nM, and more preferably ≦50 nM. In addition, the exemplified compounds of the present invention selectively bind to AR (lower Ki) relative to each of human MR, human GR, and human PR.

To demonstrate the ability of compounds of the present invention to modulate the activity of steroid hormone receptors (i.e. either agonize, partially agonize, partially antagonize, or antagonize), bioassays are performed which detect functional modulation of target gene expression in cells transiently transfected with a nuclear receptor protein and a hormone response element-reporter gene construct. The solvents, reagents, and ligands employed in the functional assay are readily available from commercial sources, or can be prepared by one of ordinary skill in the art.

Functional Assay of Steroid Hormone Nuclear Receptor Modulation:

Human embryonic kidney HEK293 cells are transfected with steroid hormone receptor and reporter gene plasmids using Fugene™ (Roche Diganostics) transfection reagent. Briefly, the reporter plasmid containing two copies of probasin ARE (androgen response element 5'GGTTCTTGGAGTACT3' (SEQ ID NO:1)) and TK (thymidine kinase) promoter upstream of the luciferase reporter cDNA, is transfected into HEK293 cells with a plasmid constitutively expressing human androgen receptor (AR) using viral CMV (cytomegalovirus) promoter. The reporter plasmid containing two copies of GRE (glucocorticoid response element 5'TGTACAGGATGTTCT'3 (SEQ ID NO:2)) and TK promoter upstream of the luciferase reporter cDNA is transfected with a plasmid constitutively expressing either human glucocorticoid receptor (GR), human mineralocorticoid receptor (MR), or human progesterone receptor (PR) using viral CMV promoter. Cells are transfected in T150 cm flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 hours and then exposed to various concentrations of test compounds ranging from about 0.01 nM to 10 µM. In the antagonist mode for the assays, low concentrations of agonist for each respective receptor are added to the media (0.25 nM dexamethasone for GR, 0.3 nM of methyltrienolone for AR, 0.05 nM of promegestone for PR and 0.05 nM aldosterone for MR). After 24 hours incubation with test compounds, cells are lysed and luciferase activity is determined using standard techniques.

Data are fitted to a four parameter-fit logistic curve fit to determine EC50 values. The percentage efficacy (compounds with saturated maximum responses) or the percent maximum stimulation (compounds with maximum responses that do not saturate) are determined relative to maximum stimulation obtained with the following reference agonists: 100 nM methyltrienolone for AR assay, with 30 nM promegestone for PR assay, with 30 nM aldosterone for MR assay and with 100 nM dexamethasone for GR assay. IC50 values may be determined similarly using antagonist mode assay data. In the antagonist mode, percent inhibitions are determined by comparing test compound activity in the presence of low concentration of agonist (0.25 nM dexamethasone for GR, 0.3 nM of methyltrienolone for AR, 0.05 nM of promegestone for PR and 0.05 nM aldosterone for MR) to the response produced by the same low concentration of agonist in the absence of test compound.

C2C12 AR/ARE Reporter Assay:

As an indicator of agonist activity in muscle tissue, the C2C12 AR/ARE reporter assay is performed. Briefly, mouse myoblast C2C12 cells are co-transfected using Fugene™ reagent. A reporter plasmid containing a GRE/ARE (glucocorticoid response element/androgen response element 5'TGTACAGGATGTTCT'3 (SEQ ID NO:3) and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 4% or 10% Fetal Bovine Serum (FBS). After a 5 hour incubation, transfected cells are trypsinized, plated in 96 well dishes in DMEM media containing 10% charcoal-stripped FBS, incubated for 2 h and then exposed to various concentrations of test compounds ranging from about 0.01 nM to 10 µM. After 48 h of incubations with compounds, cells are lysed and luciferase activity is determined by standard techniques. Data is fit to a 4 parameter-fit logistics to determine EC50 values. The % efficacy is determined versus maximum stimulation obtained with 10 nM methyltrienolone.

Functional assays of steroid hormone nuclear hormone receptor modulation similar to those described above can be readily designed by the ordinarily skilled artisan. Following a protocol essentially as described above, the exemplified compounds of the present invention display an EC50 in the C2C12 AR/ARE reporter assay of ≦1000 nM. Preferably, compounds of the present invention display an EC50 in the C2C12 AR/ARE reporter assay of ≦100 nM, and more preferably ≦50 nM.

In Vivo Model of Efficacy and Selectivity:

Male Wistar rats (12 weeks old) are castrated (gonadectomized or "GDX") according to approved procedures (Charles River Labs) and allowed to waste for eight - 10 weeks. Age-matched sham-operated mice are also prepared. (Sham-operated mice are animals that have been exposed to the same surgical procedures as castrated animals except their testes are not removed.) Animals are housed in a temperature-controlled room (24° C.) with a reversed 12 hour light/dark cycle (dark 10:00/22:00) and water and food are available ad libitum.

In order to demonstrate in vivo efficacy, compounds of the present invention are administered daily by oral gavage or subcutaneous injection to the castrated twenty week old rats (body weight about 400-450 g) Animals are randomized based on body weight prior to ascribing a test slot, such that the starting body weights of all treatment groups are within 5% of each other. Test compounds are administered to the animals using conventional vehicles. For example, 1% sodium carboxymethylcellulose (CMC)+0.25% Tween 80 in sterile $H_2O$ can be used for oral administration and 6% ethylalcohol (EtOH)+94% cyclodexitrane (CDX) can be used for subcutaneous injections. Sham operated rats treated with vehicle alone are used as a treatment positive controls whereas castrated rats treated only with vehicle are used as treatment negative control.

Test animals are dosed over a two week timeframe, orally or subcutaneously, with, for example, 0.3, 1, 3, 10 or 30 mg/kg/day of a compound of the present invention. After the two-week treatment, as an indicator of activity, the wet weight of the Levator Ani (LA) muscle in the test group is determined and compared to the wet weight of the Levator Ani from the castrated, vehicle-only control group. The wet weights of the muscle obtained in both the test group and the vehicle-only group are normalized relative to total body weight. As an indicator of tissue selective activity, the wet weight of the seminal vesicle (SV) from test animals is similarly compared to the wet weight of the seminal vesicles from the sham, vehicle-only group. Again, the wet weights of the vesicles obtained from both the test group and the vehicle-only group are normalized relative to total body weight.

In addition to the Levator Ani wet weight, the left tibia of rats are isolated during necropsy and after uncapping of the epiphysis, the soft tissue surrounding the bone is carefully removed. This sample is then placed in a solution containing 0.2% collagenase in Tris Buffer (pH 7.5). The resulting enzymatic excision of the outer periosteal layer is subjected immediately to an assay to determine alkaline phosphatase activity, an indicator of osteoblast/bone anabolic activity. Briefly, 30 µL of sample is placed in an epitube containing 200 µL of para-nitrophenyl phosphate (PNPP) substrate buffer (Pierce Cat # 37621). Purified alkaline phosphatase (Sigma Cat. # P4252) is used to make a standard curve, and the samples are read in a plate reader at $Abs_{405}$ to determine periosteal alkaline phosphatase (PALP) activity. The results obtained from both the test group and the vehicle only group may be normalized relative to total body weight.

Percent Efficacy (% Eff.) values may be determined as follows:

% Eff.=((Wet weight of LA or SV or PALP activity in test animal/test animal total body weight)/(Wet weight of LA or SV or PALP activity in control animal/control animal total body weight))×100.

Following procedures essentially as described above, the compound of Example 74 displays the following activity in the afore-mentioned rat in vivo model of efficacy and selectivity:

| Dose (mg/Kg/d), route | LA weight % Efficacy versus control (GDX) (ANOVA, p < 0.05) | SV weight % Efficacy verses control (sham) (ANOVA, p < 0.05) | PALP % Efficacy versus control (GDX) (ANOVA, p < 0.05) |
|---|---|---|---|
| 3, po | 134 | 6 | 95 |
| 10, po | 195 | 8 | 116 |
| 30, po | 186 | 14 | 107 | p.o. = oral route of administration
LA = leviator ani muscle;
SV = seminal vesicle
GDX = gonadectomized In Vivo Models of Disorders Associated with Bone Loss:

To demonstrate that compounds of the present invention have the capacity to treat disorders associated with bone loss, such as osteoporosis or osteopenia, other animal models well known to those in the art may be employed. Examples of such models are provided in Y. L. Ma et al., *Japanese Journal of Bone and Mineral Metabolism* 23 (Suppl.): 62-68 (2005); Y. L. Ma et al., *Endocrinology* 144: 2008-2015 (2003); and K. Hanada et al., *Biol. Pharm. Bull.* 26(11): 1563-1569 (2003). Particular mention is made of the Female Rat Model of Estrogen Deficiency Osteopenia induced by Ovariectomy, and the Male Rat Model of Androgen Deficiency Osteopenia induced by Orchidectomy.

Model of Estrogen Deficiency Osteopenia Induced by Ovariectomy:

Six-month-old, virgin Sprague Dawley female rats (Harlan Industries, Indianapolis Ind.), weighing about 220 g, are housed with ad libitum access to food (TD 89222 with 0.5% calcium and 0.4% phosphorus, Teklad, Madison, Wis.) and water. Bilateral ovariectomies (Ovx) are performed on the animals (except for sham-operated controls) and then randomized into treatment groups of 7-8 rats per group. Each assay typically contains at least 2 sets of controls, including sham-ovariectomy (Sham) and ovariectomized controls (Ovx) treated with vehicle. Ovx rats are permitted to lose bone for 1 month to establish osteopenia before treatment with test compound. Test compounds are administered orally via gavage to Ovx animals for 8 weeks. As a positive control, recombinant human PTH (1-38) (about 10 µg/kg/d, subcutaneously) may be given to a subset of Ovx animals. Following completion of the testing protocol, Quantitative computed tomographic (QCT, Norland/Stratec, Fort Atkinson, Wis.) is used to analyze the volumetric bone mineral density (BMD, mg/cc) of lumbar vertebra L-5 and the femur. Biomechanical analyses of three point bending on the femoral midshaft and load to failure on the proximal femur are performed using a material mechanical testing machine (model: 661.18c-01, MTS Corp, Minneapolis, Minn.) and analyzed using TestWorks 4® software (MTS Corp.)

Model of Androgen Deficiency Osteopenia Induced by Orchidectomy:

Six-month-old, Sprague Dawley male rats (Harlan Industries, Indianapolis Ind.), weighing about 485 g, are housed with ad libitum access to food (TD 89222 with 0.5% calcium and 0.4% phosphorus, Teklad, Madison, Wis.) and water. Bilateral orchidectomy (Orx) are performed on the animals (except for sham-operated controls) and then randomized into the treatment groups of 7-8 rats per group. Each assay typically contains at least 2 sets of controls, including sham-orchidectomized (Sham) and orchidectomized controls (Orx) treated with vehicle. Orx rats are permitted to lose bone for 2 months to establish osteopenia before treatment with test compound is initiated. Test compounds are administered orally via gavage to Ovx animals for 8 weeks. As a positive control, recombinant human PTH (1-38) (about 10 ug/kg/d, subcutaneously) may be given to a subset of Orx animals. Following completion of the testing protocol, the BMD of the vertebra and femur, as well as the biomechanical analyses of the femur may be performed as described above for the ovariectomized female rat model.

(See generally, Ma et al., *JBMR* 17:2256-2264 (2002), and Turner et al., *Bone* [Review] 14:595-608 (1993)).

As will be appreciated by one of ordinary skill in the art, the animal model protocols described above may be readily adapted for use in conjunction with the compounds and methods of the present invention.

The following preparations and examples further illustrate the invention and represent typical synthesis of the compounds of Formula (I), including any novel compounds, as described generally above. The reagents and starting materials are readily available to, or may be readily synthesized by, one of ordinary skill in the art. It should be understood that the Preparations and Examples are set forth by way of illustration and not limitation, and that various modifications may be made by one of ordinary skill in the art.

As used herein, "TLC" refers to thin layer chromatography; "HPLC" refers to high performance liquid chromatography; "GC/MS" refers to gas chromatography-mass spectroscopy; "LC-ES/MS" refers to liquid chromatography-electron spray mass spectroscopy; "$R_f$" refers to retention factor; "$R_t$" or "$T_R$" refers to retention time; "δ" refers to part per million down-field from tetramethylsilane; "TFA" refers to trifluoroacetic acid; "THF" refers to tetrahydrofuran; "DMF" refers to N,N-dimethylformamide; "DMSO" refers to dimethyl sulfoxide; "MTBE" refers to tert-butyl methyl ether; "$PPh_3$" refers to triphenylphosphine; "DEAD" refers to diethyl azodicarboxylate; "Pd—C" refers to palladium over carbon; $NaBH(OAc)_3$ refers to sodium triacetoxyborohydride; "Bn" refers to benzyl; "$BnNH_2$" refers to benzyl amine; "MeOH" refers to methanol; "EtOH" refers to ethanol; "EtOAc" refers to ethyl acetate; "NBS" refers to N-bromosuccinimide; AIBN refers to 2,2'-azobisisobutyronitrile; "ee" refers to enantiomeric excess.

Optical rotation is determined by standard techniques such as using a polarimeter. The R or S configuration of compounds of the invention may be determined by standard techniques such as X-ray analysis and correlation with chiral-HPLC retention time.

In general, the names for the compounds of the present invention are provided by ChemDraw® version 7.0.1.

Intermediate 1

(±)-2-(3-Oxo-cyclopentyl)-isoindole-1,3-dione

Mix cyclopentenone (100 g, 1.2 mol) and phthalimide (170 g, 1.2 mmol) in MeOH (900 mL) and stir for 18 h at ambient temperature. Stir vigorously with a mechanical stirrer and add 2 M aqueous $Na_2CO_3$ (80 mL). After approximately 2 h, a thick white precipitate will form. Stir at room temperature for 48 h. Collect the white solid by vacuum filtration and rinse with methanol. Suspend the solid in water (300 mL) and stir for 3 h. Collect the solid and dry in a vacuum oven at 40° C. overnight to give 195 g (71%) of the title compound as a white solid. $^1$H NMR (DMSO-$d_6$) δ 7.85-7.77 (m, 4H), 4.90 (m, 1H), 2.67 (ddd, 1H, J=18.5, 6.2, 1.3 Hz), 2.54 (dd, 1H, J=18.5, 9.2 Hz), 2.45 (m, 1H), 2.32-2.21 (m, 3H); MS (m/z): 230 (M+1, weak).

Intermediate 2

(±)-2-(1,3-Dioxo-1,3-dihydro-isoindol-2-yl)-1,2,3,4-tetrahydro-cyclopenta[b]indole-7-carbonitrile Mix (±)-2-(3-oxo-cyclopentyl)-isoindole-1,3-dione (12.7 g, 55.3 mmol) and 4-cyanophenylhydrazine-HCl (8.53 g, 50.3 mmol) in HOAc (200 mL) and 4N HCl dioxane (50 mL). Using mechanical stirring, heat the reaction to 90° C. for 18 h, then add additional 4N HCl dioxane (20 mL). Heat the reaction to 100° C. for 18 h. Dilute the reaction mixture with water (600 mL) and collect a black solid by vacuum filtration. Sonicate the solid with MeOH (200 mL), then collect and dry in a vacuum oven to give 10.94 g (66%) of a gray-brown solid. MS (m/z): 328 (M+1), 326 (M−1).

Intermediate 3

(±)-2-(7-Trifluoromethoxy-1,2,3,4-tetrahydro-cyclopenta[b]indol-2-yl)-isoindole-1,3-dionene Mix (4-trifluoromethoxy-phenyl)-hydrazine hydrochloride (1.5 g, 6.56 mmol) and (±)-2-(3-oxo-cyclopentyl)-isoindole-1,3-dione in EtOH (20 mL) and heat to reflux for 14 hours. Concentrate the reaction mixture in vacuo and dilute the residue with $Et_2O$ (150 mL). Place the mixture in an ultrasonic bath for 10 min, then filter off a solid. Concentrate the filtrate to give the crude product. Purify the material on silica gel (120 g) using 10-60% EtOAc/hexanes to give 520 mg (22%) of the title compound as a yellow solid. $^1$H-NMR (DMSO-$d_6$) δ 11.22 (s, 1H), 7.85 (m, 4H), 7.38 (d, 1H, J=8.8 Hz), 7.28 (d, 1H, J=1.3 Hz), 6.96 (dd, 1H, J=8.8, 1.3 Hz), 5.41 (m, 1H), 3.38-3.11 (m, 4H).

Intermediate 4

(±)-2-Amino-1,2,3,4-tetrahydro-cyclopenta[b]indole-7-carbonitrile

In a three neck round bottomed flask, equipped with a mechanical stirrer, prepare a mixture of THF (3100 ml) and ethanol (550 ml). To this mixture add crude 2-(1,3-dioxo-1,3-dihydro-isoindol-2-yl)-1,2,3,4-tetrahydro-cyclopenta[b] indole-7-carbonitrile (170 g, 0.52 mol) and stir for 15 min. Add hydrazine hydrate (90 ml, 1.9 mol) and stir the mixture at room temperature for 16 h. Check by LC/MS to confirm that no starting material remains. Filter the crude reaction in vacuo and wash the solid with THF (2×200 mL). Collect the mother liquors and remove the solvent under vacuum. Purify by silica gel filtration (1.5" high, very wide $SiO_2$ pad) using (2 M $NH_3$/MeOH)/$CH_2Cl_2$ (3-10%). Collect the fractions containing product and remove the solvent. Add acetonitrile (180 ml) and reflux the mixture for 15 min and then cool to room temperature. Collect a brown solid by filtration and dry in vacuo overnight at 40° C. to give the racemic title compound, 55 g (60%). GC-MS: 198 (M+), 196 (M−);

NOTE: At this point either separate the enantiomers of the racemic amine or continue the synthesis with racemic material and perform a chiral prep-HPLC separation of the final compounds.

Intermediate 4a (S)-2-amino-1,2,3,4-tetrahydro-cyclopenta[b]indole-7-carbonitrile

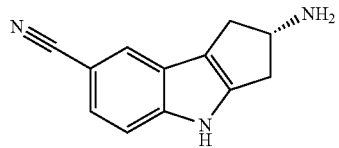

In a 2 L flask equipped with mechanical stirrer and condenser, add ethanol (945 ml) and (±)-2-amino-1,2,3,4-tetrahydro-cyclopenta[b]indole-7-carbonitrile (40 g, 0.203 mmol). Stir the mixture and heat to 60-65° C. until complete solution is achieved. Add D-pyroglutamic acid (28.4 g, 0.192 mmol) and water (55 ml). Heat the mixture to reflux for 20 min. Cool to 40-45° C. over 90 min. Stir at 40-45° C. for one hour, and then cool to 24° C. over 2 h. Stir at this temperature for two additional hours. Isolate a crystalline solid by filtration and wash with a mixture of EtOH/water (95:5) (3×50 mL). Dry the solid in vacuo at 50° C. overnight to give 23 g pyroglutamic acid salt.

Free base isolation: Add the pyroglutamic acid salt to water (150 mL) and stir until complete solution is achieved. Filter through a diatomaceous earth pad. Collect the aqueous solution and adjust the pH to 9 adding aqueous concentrated ammonia. Collect an off-white solid by filtration and dry in vacuo at 50° C. overnight to give 13.5 g (35%) (S)-2-amino-1,2,3,4-tetrahydro-cyclopenta[b]indole-7-carbonitrile, ≧94% ee (column, Chiracel OJ (4.6×250 mm; 10 μm); solvent, 20% EtOH/(0.2% dimethylethylamine/hexanes), checked against racemic mixture). Specific rotation: $[a]_D^{25}$ −68.3° (MeOH).

Intermediate 4b (R)-2-amino-1,2,3,4-tetrahydro-cyclopenta[b]indole-7-carbonitrile Prepare the title compound essentially as described for Intermediate 4a, employing L-pyroglutamic acid. The product (97% ee) has a specific rotation result: $[a]_D^{25}$ +63° (EtOH).

Intermediate 5

(±)-7-Trifluoromethoxy-1,2,3,4-tetrahydro-cyclopenta[b]indol-2-ylamine

Prepare essentially as described for Intermediate 4, using (±)-2-(7-trifluoromethoxy-1,2,3,4-tetrahydro-cyclopenta[b]indol-2-yl)-isoindole-1,3-dionene. MS (m/z): 257 (M+1), 255 (M−1).

Intermediate 6

(±)-(7-Cyano-1,2,3,4-tetrahydro-cyclopenta[b]indol-2-yl)-carbamic acid isopropyl ester Under nitrogen, mix (±)-2-amino-1,2,3,4-tetrahydro-cyclopenta[b]indole-7-carbonitrile (7.0 g, 35.5 mmol) with diisopropylethylamine (7.4 mL, 42.6 mmol) in $CH_2Cl_2$ (70 mL). Add isopropyl chloroformate (1.0 M in toluene, 42.6 mL, 42.6 mmol) and stir overnight at room temperature. Dilute with water (100 mL) and ethyl ether (50 mL), stir for 10 min and collect the solid. After drying, obtain 7.42 g (61%) of the title compound as a tan solid. MS (m/z): 284 (M+1), 282 (M−1).

Prepare the intermediates in Table 1 essentially as described for the preparation of Intermediate 6 using the appropriate acid chloride, chloroformate, or dialkyl dicarbonate, with triethylamine and diisopropylethylamine as base interchangeably.

TABLE 1

| Intermediate | Chemical Name | MS (m/z) |
|---|---|---|
| 7 | (±)-N-(7-Cyano-1,2,3,4-tetrahydro-cyclopenta[b]indol-2-yl)-isobutyramide | 268 (M + 1) 266 (M − 1) |
| 8 | (±)-Cyclopropanecarboxylic acid (7-cyano-1,2,3,4-tetrahydro-cyclopenta[b]indol-2-yl)-amide | 266 (M + 1) 264 (M − 1) |
| 9 | (±)-(7-Cyano-1,2,3,4-tetrahydro-cyclopenta[b]indol-2-yl)-carbamic acid tert-butyl ester | No data |
| 10 | (±)-(7-Trifluoromethoxy-1,2,3,4-tetrahydro-cyclopenta[b]indol-2-yl)-carbamic acid isopropyl ester | 343 (M + 1) |
| 11 | (±)-(7-Cyano-1,2,3,4-tetrahydro-cyclopenta[b]indol-2-yl)-carbamic acid ethyl ester | 270 (M + 1) 268 (M − 1) |
| 12 | (R)-Cyclopropanecarboxylic acid (7-cyano-1,2,3,4-tetrahydro-cyclopenta[b]indol-2-yl)-amide | No data |
| 13 | (S)-Cyclopropanecarboxylic acid (7-cyano-1,2,3,4-tetrahydro-cyclopenta[b]indol-2-yl)-amide | No data |
| 14 | (R)-(7-Cyano-1,2,3,4-tetrahydro-cyclopenta[b]indol-2-yl)-carbamic acid isopropyl ester | 284 (M + 1) 282 (M − 1) |
| 15 | (S)-(7-Cyano-1,2,3,4-tetrahydro-cyclopenta[b]indol-2-yl)-carbamic acid isopropyl ester | 284 (M + 1) 282 (M − 1) |
| 16 | (R)-(7-Cyano-1,2,3,4-tetrahydro-cyclopenta[b]indol-2-yl)-carbamic acid tert-butyl ester | 296 (M − 1) |
| 17* | (S)-(7-Cyano-1,2,3,4-tetrahydro-cyclopenta[b]indol-2-yl)-carbamic acid tert-butyl ester | No data |

*Alternatively, obtain Intermediate 17 by chiral chromatography of Intermediate 9.

Intermediate 18

(±)-N-[7-(Methoxyimino-methyl)-1,2,3,4-tetrahydro-cyclopenta[b]indol-2-yl]-isobutyramide Mix (±)-N-[7-cyano-1,2,3,4-tetrahydro-cyclopenta[b]indol-2-yl]-isobutyramide (5 g, 18.7 mmol) and Al—Ni catalyst (15 g) in water/96% formic acid, 1/10 (110 mL). Reflux for 18 h, add Al—Ni catalyst (13 g) and reflux another 5 h. Cool and dilute with MeOH and filter off the inorganics. Concentrate the filtrate, add EtOH (200 mL) and sonicate for 15 min. Filter insoluble material and to the crude aldehyde solution add O-methoxyamine-HCl (120 mmol) dissolved in water (25 mL) and make the mixture basic (pH=9-12) with 5.0 N NaOH. Stir at room temperature for 18 h and remove most of the solvent under reduced pressure. Mix the residue with water and sonicate for 30 min. Isolate 4.39 g of a brown solid. Purify the material on silica gel using 30-100% EtOAc/hexane to give 530 mg (10%) title compound as a pale yellow solid. MS (m/z): 300 (M+1), 298 (M−1).

Intermediate 19

(R)—N-[7-(Methoxyimino-methyl)-1,2,3,4-tetrahydro-cyclopenta[b]indol-2-yl]-2,2-dimethyl-propionamide Combine dichloromethane (15 ml) and (R)-[7-cyano-1,2,3,4-tetrahydro-cyclopenta[b]indol-2-yl]-carbamic acid tert-butyl ester (2 g, 6.73 mmol) and stir for 10 min under nitrogen at room temperature. Add diisobutylaluminum hydride (1 M solution in methylene chloride, 14.1 ml; 14.1 mmol) dropwise over 15 min. Add ethyl acetate (30 mL) to the reaction mixture and stir at room temperature for 1 h. Add a 20% aqueous solution of sodium tartrate (30 mL) and stir for 1 h at room temperature. Separate the organic layer and extract the aqueous layer with ethyl acetate (2×15 mL). Combine and dry ($Na_2SO_4$) organic layers, filter and concentrate to give 2.2 g [(R)-7-formyl-1,2,3,4-tetrahydro-cyclopenta[b]indol-2-yl]-carbamic acid tert-butyl ester. Purify by chromatography on silica gel using methylene chloride/acetone (95/5) to give 1.3 g (64%). MS (m/z): 301 (M+1).

To a 100 mL round-bottom flask add [(R)-7-formyl-1,2,3,4-tetrahydro-cyclopenta[b]indol-2-yl]-carbamic acid tert-butyl ester (1.00 g; 3.33 mmol), ethanol (10 ml), potassium carbonate (552 mg, 4 mmol), and O-methylhydroxylamine hydrochloride (334 mg; 4.0 mmol). Stir the mixture at room temperature for 1 h. Remove the solvent in vacuo and add water (15 mL). Stir the mixture 30 min and filter to give 790 mg (72%). MS (m/z): 330 (M+1).

Intermediate 20

2-Bromomethyl-6-fluoro-pyridine

Add NBS (35.6 g, 0.20 mole) to a solution of 6-fluoro-2-methylpyridine (20 mL, 0.19 mole) in EtOAc (400 mL) at room temperature. When the temperature reaches 45° C., add AIBN (400 mg, 2.4 mmol). Heat the mixture at 65° C. for 6 h, then cool to room temperature and add hexane (1 L). Remove the white precipitate by filtration and wash the solid with hexane/EtOAc (1:1). Wash the filtrate with small amounts of aqueous $Na_2S_2O_3$, $NaHCO_3$, and brine. Dry the organics ($Na_2SO_4$), filter, then remove most of the solvent under vacuum at room temperature. Transfer the remaining solution to a distillation set-up. Remove the remaining solvent by distilling at atmospheric pressure, followed by the unreacted starting material at 80 mm (bp ca 70° C.; 11.2 g) and then the title product at 1 mm (bp ca 75° C.; 12.1 g, 32%). NMR (300 MHz; $CDCl_3$): 7.82 (1H; dd); 7.35 (1H; dd); 6.90 (1H; dd); 4.50 (2H; s).

Intermediate 21

2-(3-Bromomethyl-pyridin-2-yl)-isoindole-1,3-dione

Prepare the title compound using the method as described by Goswami, S.; et al. *J. Am. Chem. Soc.* 1989, 111, 3425-

3426 and as exemplified by Graczyk, P. WO2004013139, 2004, starting with 2-amino-3-picoline and phthalic anhydride, followed by bromination with NBS, to yield the product in 33% yield as a white solid. MS (m/z): 317, 319 (M+1).

Intermediate 22

3-Bromomethyl-isothiazole

Prepare 3-methylisothiazole from commercially available 5-amino-3-methyl isothiazole hydrochloride by the procedure of Buttimore, D.; et al. *J. Chem. Soc.* 1963, 2032-2039. Reflux a mixture of 3-methylisothiazole (3.61 g, 36.6 mmol), N-bromosuccinimide (6.8 g, 38.2 mmol) and 1,1-azobis(cyclohexanecarbonitrile) (0.18 g, 0.73 mmol) in $CCl_4$ (100 mL) for 18 h. Cool and remove the succinimide by-product by filtration. Concentrate the filtrate and purify using chromatography on silica gel with EtOAc/hexane (1/5) to provide 2.78 g (42.9%) of the product. $^1$H NMR (400 MHz, $CDCl_3$) δ 8.63 (d, J=5.1 Hz, 1H), 7.34 (d, J=5.1 Hz, 1H), 4.59 (s, 2H).

Intermediate 23

5-Bromo-3-bromomethyl-isothiazole

Prepare 5-bromo-3-methylisothiazole according to the method of Adams, A.; Slack, R. *J. Chem. Soc.* 1959, 3061-3072. Prepare the title compound as essentially described for Intermediate 22 using NBS and 5-bromo-3-methylisothiazole.

Intermediate 24

2-Bromomethyl-6-difluoromethyl-pyridine

Slowly add bis-(2-methoxyethyl)aminosulfur trifluoride (9.2 mL, 50 mmol) to 6-methyl-2-pyridinecarboxaldehyde (2.6 g, 21.5 mmol) in $CH_2Cl_2$ (25 mL). After 18 h, carefully pour into a beaker containing saturated $NaHCO_3$ (300 mL). Shake with water/$CH_2Cl_2$ and separate. Dry the organic layer ($Na_2SO_4$) and concentrate to give 2.11 g brown oil. Purify on silica gel (50% EtOAc/hexane) to give 1.16 g (38%) 2-methyl-6-difluoromethyl-pyridine as a yellow-tan oil. Dissolve (1.0 g, 7 mmol) in $CCl_4$ (30 mL) and add NBS (1.2 g, 6.8 mmol) and AIBN (100 mg). Reflux for 4 h, filter and concentrate. Purify the resulting residue on silica gel using 5-10% EtOAc/hexane over 30 min to provide 670 mg (43%). GC/MS 221+223.

Intermediate 25

2-Chloromethyl-3-chloropyrazine

Prepare the title compound using the chlorination procedure as essentially described by Jeromin, G. E.; et al., DE3519364, 1986, and Russell, M. G. N.; et al. *J. Med. Chem.* 2005, 48, 1367-1383. Dissolve 2-methyl-3-chloropyrazine (24.3 g, 189 mmol) in $CHCl_3$ (100 mL). Add benzamide (100 mg, 0.8 mmol) and heat to reflux. At reflux, add solid trichloroisocyanuric acid (17.6 g, 75.6 mmol) and continue to reflux for 96 h. Cool and filter through 200 g silica gel, eluting with methylene chloride. Purify by silica gel chromatography using a gradient of 35% chloroform/hexane to 60% chloroform/hexane over one hour. Obtain the title compound as a colorless oil, 5.39 g pure title compound and 9.4 g that is >70% desired product. $^1$H-NMR ($CDCl_3$) δ 8.50 (d, 1H, J=2.2 Hz), 8.37 (d, 1H, J=2.6 Hz), 4.80 (s, 2H), 2.50 (s, 3H); GC/MS M=162+164.

Prepare Intermediates 26-29 by essentially following the procedure described for Intermediate 25 using 2,3-dimethylpyrazine, 2-chloro-4-methylpyridine, 2-methylthiazole, and 3-methylpyridazine.

| Intermediate number | Chemical Name |
|---|---|
| 26 | 2-Chloromethyl-3-methyl-pyrazine |
| 27 | 2-Chloro-4-chloromethyl-pyridine |
| 28 | 2-Chloromethylthiazole |
| 29 | 3-Chloromethyl-pyridazine |

Prepare Intermediates 30 and 31 by essentially following the procedure as described by Newkome, G. R.; et al. *Synthesis* 1984, 676-679, using 2-methylpyrazine and 2,5-dimethylpyrazine and N-chlorosuccinimide (NCS).

| | |
|---|---|
| 30 | 2-Chloromethylpyrazine |
| 31 | 2-Chloromethyl-5-methyl-pyrazine |

Intermediate 32

[1,2,5]Thiadiazole-3-carboxylic Acid

Prepare the title compound according to the procedure of Weinstock, L. M.; et al. *J. Org. Chem.* 1967, 32, 2823-2828.

Intermediate 33

[1,2,5]Thiadiazol-3-ylmethanol

Mix [1,2,5]thiadiazole-3-carboxylic acid (6.00 g, 46.1 mmol) and oxalyl chloride (11.7 g, 8.04 mL, 92.2 mmol) in $CH_2Cl_2$ (150 mL). To this heterogeneous slurry, add 10 drops of DMF and stir at room temperature. The reaction mixture will bubble and gradually become translucent within one hour. After one hour, concentrate the reaction mixture in vacuo to give the acid chloride as a brown oil.

Dissolve the acid chloride in EtOH (50 mL) and stir at room temperature for one hour, then concentrate in vacuo to give the ethyl ester as a brown oil.

Dissolve the ethyl ester in THF (100 mL) and add $LiBH_4$ (2.0 M solution in THF, 46.1 mL, 92.2 mmol). Stir the reaction mixture at room temperature for 18 h. Pour the reaction mixture into aqueous $NH_4Cl$ (400 mL) and extract into EtOAc (3×150 mL). Dry the organics ($MgSO_4$) and concentrate in vacuo to give 4.41 g crude product as a yellow oil. Purify on silica gel (40 g) using 30% EtOAc/hexanes to give 3.71 g (69%) of the title compound as a yellow oil. $^1$H-NMR ($CDCl_3$) δ 8.59 (s, 1H), 5.00 (s, 2H).

Intermediate 34

Methanesulfonic acid [1,2,5]thiadiazol-3-ylmethyl ester

Prepare the title compound according to the procedure of Yamamoto, H.; et al. *Bioorg. Med. Chem.* 2001, 9, 465-475.

Intermediate 35

3-Hydroxymethyl-4,5-dichloroisothiazole

Add LiBH$_4$ (2.0 M in THF, 10 mL, 20 mmol) to a solution of 4,5-dichloro-isothiazole-3-carboxylic acid methyl ester (2.1 g, 10 mmol) in THF (60 mL). Stir at room temperature for one hour and then cool to 0° C. Carefully quench the reaction mixture with water (10 mL), then saturated aqueous NH$_4$Cl (50 mL). Extract into EtOAc (100 mL), then dry (MgSO$_4$), filter, and concentrate the organics to give 540 mg crude product as an orange syrup. Purify the syrup on silica gel (40 g) using 5-30% EtOAc/hexanes to give 310 mg (17%) of the title compound as a white solid. $^1$H-NMR (DMSO-d$_6$) δ 5.55 (t, 1H, J=5.9 Hz), 4.52 (d, 2H, J=6.2 Hz).

Intermediate 36

2-Chloro-4-hydroxymethylthiazole

Prepare 2-chloro-thiazole-4-carboxylic acid ethyl ester essentially as described by Erlenmeyer, H.; et al. *Helv. Chim. Acta* 1944, 27, 1432-1436. Prepare the title compound by essentially following the procedure as described for Intermediate 35, using 2-chloro-thiazole-4-carboxylic acid ethyl ester. MS (m/z): 150 (M+1); $^1$H-NMR (CDCl$_3$) δ 7.16 (t, 1H, J=1.0 Hz), 4.75 (d, 2H, J=0.9 Hz), 2.48 (s, 1H).

Intermediate 37

2-Amino-5-methyl-thiazole-4-carboxylic acid ethyl ester

Prepare the title compound according to the procedure of Hénichart. J.-P.; et al. *Heterocycles* 1991, 32, 693-701.

Intermediate 38

5-Methyl-thiazole-4-carboxylic acid ethyl ester

In a 3-neck round bottom flask mix 2-amino-5-methyl-thiazole-4-carboxylic acid ethyl ester (62.9 g, 338 mmol) and THF (630 mL). Heat to reflux and treat the reaction mixture with isoamyl nitrile (52.6 g, 60.1 mL, 449 mmol) dropwise. Upon completion of the addition, stir the reaction at reflux for 1 h, then concentrate the reaction mixture by rotavap (hi-vac) to give 70 g crude product as a thick orange oil. Purify on silica gel (400 g, 20-45% EtOAc/hexanes) to afford 39.47 g (68%) of the title compound as a yellow solid. LC-ES/MS m/z 172 (M+1), T$_R$=1.5 min.

Intermediate 39

5-Bromomethyl-thiazole-4-carboxylic acid ethyl ester

Heat to reflux a mixture of 5-methyl-thiazole-4-carboxylic acid ethyl ester (4.87 g, 28.5 mmol) and N-bromosuccinimide (5.06 g, 28.5 mmol) in CCl$_4$ (100 mL) by irradiation with a 275 watt tungsten sun lamp. After 3 h, cool to room temperature and filter off a tan solid. Concentrate the filtrate by rotavap to give 6.42 g crude product as an orange oil. Purify on silica gel [115 g, 0-15% (2M NH$_3$/MeOH)/(1:1 CH$_2$Cl$_2$/hexanes)] to give 3.61 g (51%) of the title compound as a yellow solid. LC-ES/MS m/z 250, 252 (M+1), T$_R$=2.0 min (86%). Starting material: m/z 172 (M+1), T$_R$=1.7 min (14%).

Example 1

(±)-N-[7-Cyano-4-(6-fluoro-pyridin-2-ylmethyl)-1,2,3,4-tetrahydrocyclo-penta[b]indol-2-yl]isobutyramide

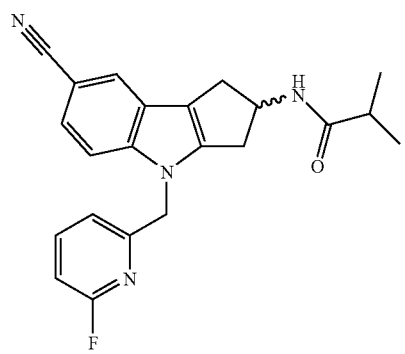

Mix (±)-N-(7-cyano-1,2,3,4-tetrahydro-cyclopenta[b]indol-2-yl)-isobutyramide (6.28 g, 18.8 mmol), 6-fluoro-2-bromomethylpyridine (3.93 g, 20.7 mmol), and Cs$_2$CO$_3$ (12.25 g, 37.6 mmol) in DMF (25 mL). Heat the reaction at 50° C. for 18 h. Cool, dilute with EtOAc, and wash with water (3×200 mL). Dry the organic layer (MgSO$_4$) and concentrate to give 7.1 g crude material. Purify by silica gel chromatography (5-20% EtOAc/CH$_2$Cl$_2$). Obtain 4.0 g (56%) yellow-tan solid. MS (m/z): 377 (M+1), 375 (M−1).

Example 1a & 1b

(R)- and (S)—N-[7-Cyano-4-(6-fluoro-pyridin-2-ylmethyl)-1,2,3,4-tetrahydro-cyclopenta[b]indol-2-yl]-isobutyramide Separate enantiomers of Example 1 by chiral chromatography using Chiralpak AD-H (MeOH).
Isomer 1 (R): 1.67 g 99% ee, HPLC: R$_f$=3.44 (96.5%), $^1$H-NMR (DMSO-d$_6$) δ 8.22 (d, 1H, J=7.5 Hz), 7.96-7.88 (m, 2H), 7.62 (d, 1H, J=8.3 Hz), 7.38 (dd, 1H, J=8.4, 1.8 Hz), 7.07 (td, 2H, J=10.9, 3.9 Hz), 5.44 (dd, 2H, J=19.2, 16.5 Hz), 4.86 (m, 1H), 3.28-3.12 (m, 2H), 2.69-2.61 (m, 2H), 2.32 (m, 1H), 0.97 (t, 6H, J=6.4 Hz). Isomer 2 (S): 1.45 g 98.9% ee, HPLC: R$_f$=3.44 min (100%), $^1$H-NMR (DMSO-d$_6$) is identical to that of Isomer 1.

Example 2

(±)-(7-Cyano-4-pyrimidin-4-ylmethyl-1,2,3,4-tetrahydrocyclopenta[b]indol-2-yl)-carbamic acid isopropyl ester

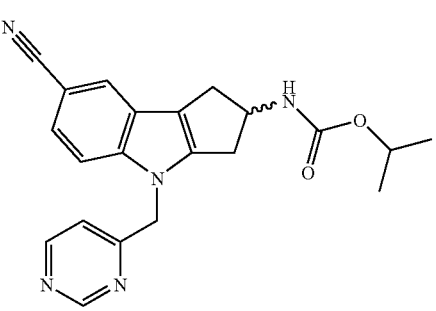

To a suspension of pyrimidin-4-ylmethanol (250 mg, 2.27 mmol) in CH$_2$Cl$_2$ (12 mL), add N,N-diisopropylethylamine (475 mg, 640 µL, 3.68 mmol) and cool to 0° C. under nitrogen. Add methanesulfonyl chloride (275 mg, 186 µL, 2.40 mmol) and warm up to room temperature. After stirring at room temperature for 1 h, load the reaction mixture onto a Varian ChemElut CE1005 solid-phase extraction cartridge (Varian part number 12198006) which has been pre-treated with water (2 mL). Elute CH$_2$Cl$_2$ (30 mL) through the cartridge, collecting and concentrating the organic eluent. Add DMF to the eluent, and concentrate in vacuo to give a DMF solution of the mesylate. To this solution, add (±)-(7-cyano-1,2,3,4-tetrahydrocyclopenta[b]indol-2-yl)-carbamic acid isopropyl ester (495 mg, 1.75 mmol), Cs$_2$CO$_3$ (1.14 g, 3.5 mmol), and DMF (10 mL). Heat the mixture to 50° C. for 18 h in a sealed vial. Dilute the reaction with EtOAc (100 mL) and wash the organics with water (3×60 mL). Dry the organic layer over MgSO$_4$, filter, and concentrate to give 631 mg of the crude product as a red oil. Purify the oil on 40 g silica gel [40-90% EtOAc/(1:1 CH$_2$Cl$_2$/hexanes)] to give 487 mg (74%) of the title compound as a white solid. LCMS 92% @ 4.34 min (m/z): 376 (M+1), 374 (M−1), 420 (M+HCO$_2^-$).

Example 3

(S)-7-(Cyano-4-thiazol-5-ylmethyl-1,2,3,4-tetrahydro-cyclopenta[b]indol-2-yl)-carbamic acid isopropyl ester

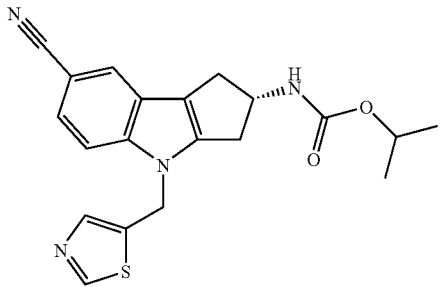

Add N,N-diisopropylethylamine (2.39 g, 3.2 mL, 18.5 mmol) and methanesulfonyl chloride (1.27 g, 864 µL, 11.1 mmol) to a chilled (0° C.) solution of 5-(hydroxymethyl)thiazole (1.22 g, 10.6 mmol) in CH$_2$Cl$_2$ (50 mL) under nitrogen. Stir the reaction at room temperature for 18 h. Add water (30 mL), separate the layers, and dry the organics over MgSO$_4$. Filter and add DMF (10 mL) to the organic layer. Concentrate under vacuum leaving a solution of the mesylate in DMF. To this solution, add additional DMF (40 mL), (S)-7-(cyano-1,2,3,4-tetrahydro-cyclopenta[b]indol-2-yl)-carbamic acid isopropyl ester (2.50 g, 8.82 mmol), and Cs$_2$CO$_3$ (5.57 g, 17.6 mmol). Stir at room temperature for 72 h. Dilute the reaction mixture with EtOAc (300 mL), wash the organics with water (3×130 mL), then brine (100 mL). Dry (MgSO$_4$), filter, and concentrate the organics to give 3.8 g of crude product as a yellow oil. Purify on silica gel [120 g, 30-60% EtOAc/(1:1 CH$_2$Cl$_2$/hexanes)] to give 2.22 g (66%) of the title compound as a white solid. LCMS 100% @ 4.46 min (m/z) 381 (M+H), 425 (M+HCO$_2^-$).

Use the procedure as described above in Example 2 or 3 to convert the following alcohols to the mesylates: 2-hydroxymethylpyrimidine, 3-hydroxymethyl-4,5-dichloroisothiazole, 2-chloro-4-hydroxymethylthiazole, 2-hydroxmethylthiazole, and 5-hydroxymethylthiazole.

Using the appropriately substituted 1,2,3,4-tetrahydrocyclopenta[b]indole, prepare Examples 4-53 and Intermediate 40-41, in Table 2, essentially according to the procedures described in Examples 1 and 2, using the appropriate heteroarylmethyl halide or heteroarylmethyl mesylate, which have been described above or are commercially available. Prepare chiral material from the corresponding chiral 1,2,3,4-tetrahydrocyclopenta[b]indole prepared above or separate the racemic material as essentially described in Example 1a and 1b.

TABLE 2

| Example | Chemical Name | MS (m/z) |
| --- | --- | --- |
| 4 | (R)-[7-Cyano-4-(6-fluoro-pyridin-2-ylmethyl)-1,2,3,4-tetrahydro-cyclopenta[b]indol-2-yl]-carbamic acid isopropyl ester | 393 (M + 1) |
| 5 | (S)-[7-Cyano-4-(6-fluoro-pyridin-2-ylmethyl)-1,2,3,4-tetrahydro-cyclopenta[b]indol-2-yl]-carbamic acid isopropyl ester | 393 (M + 1) |
| 6* | (±)-[7-Cyano-4-(3-hydroxy-pyridin-2-ylmethyl)-1,2,3,4-tetrahydro-cyclopenta[b]indol-2-yl]-carbamic acid isopropyl ester | 391 (M + 1) |
| 7 | (±)-(7-Cyano-4-pyridin-2-ylmethyl-1,2,3,4-tetrahydro-cyclopenta[b]indol-2-yl)-carbamic acid ethyl ester | 361 (M + 1) |
| 8 | (±)-[7-Cyano-4-(6-difluoromethyl-pyridin-2-ylmethyl)-1,2,3,4-tetrahydro-cyclopenta[b]indol-2-yl]-carbamic acid isopropyl ester | 425 (M + 1) |
| 9 | (±)-(7-Cyano-4-thiazol-4-ylmethyl-1,2,3,4-tetrahydro-cyclopenta[b]indol-2-yl)-carbamic acid isopropyl ester | 381 (M + 1), 425 (M + HCO$_2^-$) |
| 10 | (±)-[7-Cyano-4-(2-methyl-thiazol-4-ylmethyl)-1,2,3,4-tetrahydro-cyclopenta[b]indol-2-yl]-carbamic acid isopropyl ester | 395 (M + 1), 439 (M + HCO$_2^-$) |
| 11 | (±)-(7-Cyano-4-pyrimidin-2-ylmethyl-1,2,3,4-tetrahydro-cyclopenta[b]indol-2-yl)-carbamic acid isopropyl ester | 376 (M + 1) |
| 12 | (±)-[4-(6-Fluoro-pyridin-2-ylmethyl)-7-trifluoromethoxy-1,2,3,4-tetrahydro-cyclopenta[b]indol-2-yl]-carbamic acid isopropyl ester | 452 (M + 1), 496 (M + HCO$_2^-$) |
| 13 | (±)-(7-Cyano-4-pyrazin-2-ylmethyl-1,2,3,4-tetrahydro-cyclopenta[b]indol-2-yl)-carbamic acid isopropyl ester | 376 (M + 1), 420 (M + HCO$_2^-$) |
| 14** | (R)-(7-Cyano-4-pyridin-2-ylmethyl-1,2,3,4-tetrahydro-cyclopenta[b]indol-2-yl)-carbamic acid ethyl ester | 361 (M + 1) |
| 15** | (S)-(7-Cyano-4-pyridin-2-ylmethyl-1,2,3,4-tetrahydro-cyclopenta[b]indol-2-yl)-carbamic acid ethyl ester | 361 (M + 1) |
| 16 | (±)-(7-Cyano-4-thiazol-4-ylmethyl-1,2,3,4-tetrahydro-cyclopenta[b]indol-2-yl)-carbamic acid ethyl ester | 367 (M + 1), 411 (M + HCO$_2^-$) |
| 17 | (±)-(7-Cyano-4-pyridazin-3-ylmethyl-1,2,3,4-tetrahydro-cyclopenta[b]indol-2-yl)-carbamic acid isopropyl ester | 367 (M + 1), 411 (M + HCO$_2^-$) |
| 18 | (±)-(7-Cyano-4-pyrazin-2-ylmethyl-1,2,3,4-tetrahydro-cyclopenta[b]indol-2-yl)-carbamic acid ethyl ester | 367 (M + 1), 411 (M + HCO$_2^-$) |
| 19 | (±)-[4-(5-Bromo-isothiazol-3-ylmethyl)-7-cyano-1,2,3,4-tetrahydro-cyclopenta[b]indol-2-yl]-carbamic acid isopropyl ester | 459, 461 (M + 1) |
| 20 | (±)-(7-Cyano-4-isothiazol-3-ylmethyl-1,2,3,4-tetrahydro-cyclopenta[b]indol-2-yl)-carbamic acid isopropyl ester | 381 (M + 1) |
| 21 | (±)-[4-(2-Chloro-thiazol-4-ylmethyl)-7-cyano-1,2,3,4-tetrahydro-cyclopenta[b]indol-2-yl]-carbamic acid isopropyl ester | 415 (M + 1), 459 (M + HCO$_2^-$) |
| 22 | (R)-(7-Cyano-4-pyrazin-2-ylmethyl-1,2,3,4-tetrahydro-cyclopenta[b]indol-2-yl)-carbamic acid isopropyl ester | 376 (M + 1), 420 (M + HCO$_2^-$) |
| 23 | (S)-(7-Cyano-4-pyrazin-2-ylmethyl-1,2,3,4-tetrahydro-cyclopenta[b]indol-2-yl)-carbamic acid isopropyl ester | 376 (M + 1), 420 (M + HCO$_2^-$) |

TABLE 2-continued

| Example | Chemical Name | MS (m/z) |
|---|---|---|
| 24 | (R)-(7-Cyano-4-thiazol-4-ylmethyl-1,2,3,4-tetrahydro-cyclopenta[b]indol-2-yl)-carbamic acid isopropyl ester | 381 (M + 1), 425 (M + HCO$_2^-$) |
| 25 | (S)-(7-Cyano-4-thiazol-4-ylmethyl-1,2,3,4-tetrahydro-cyclopenta[b]indol-2-yl)-carbamic acid isopropyl ester | 381 (M + 1), 425 (M + HCO$_2^-$) |
| 26 | (R)-(7-Cyano-4-pyrimidin-4-ylmethyl-1,2,3,4-tetrahydro-cyclopenta[b]indol-2-yl)-carbamic acid isopropyl ester | 376 (M + 1), 374 (M − 1) |
| 27 | (S)-(7-Cyano-4-pyrimidin-4-ylmethyl-1,2,3,4-tetrahydro-cyclopenta[b]indol-2-yl)-carbamic acid isopropyl ester | 376 (M + 1), 374 (M − 1) |
| 28 | (±)-[7-Cyano-4-(3-methyl-pyrazin-2-ylmethyl)-1,2,3,4-tetrahydro-cyclopenta[b]indol-2-yl]-carbamic acid isopropyl ester | 390 (M + 1), 412 (M + Na) |
| 29 | (±)-[4-(2-Chloro-pyrimidin-4-ylmethyl)-7-cyano-1,2,3,4-tetrahydro-cyclopenta[b]indol-2-yl]-carbamic acid isopropyl ester | 410 (M + 1) |
| 30 | (±)-[7-Cyano-4-(4,5-dichloro-isothiazol-3-ylmethyl)-1,2,3,4-tetrahydro-cyclopenta[b]indol-2-yl]-carbamic acid isopropyl ester | 449 (M + 1) 447 (M − 1) |
| 31 | (±)-(7-Cyano-4-thiazol-2-ylmethyl-1,2,3,4-tetrahydro-cyclopenta[b]indol-2-yl)-carbamic acid isopropyl ester | 381 (M + 1), 403 (M + Na) |
| 32 | (±)-(7-Cyano-4-thiazol-5-ylmethyl-1,2,3,4-tetrahydro-cyclopenta[b]indol-2-yl)-carbamic acid isopropyl ester | 381 (M + 1), 425 (M + HCO$_2^-$) |
| 33 | (±)-[4-(3-Chloro-pyrazin-2-ylmethyl)-7-cyano-1,2,3,4-tetrahydro-cyclopenta[b]indol-2-yl]-carbamic acid isopropyl ester | 410 (M + 1), 408 (M − 1) |
| 34 | (±)-(7-Cyano-4-[1,2,5]thiadiazol-3-ylmethyl-1,2,3,4-tetrahydro-cyclopenta[b]indol-2-yl)-carbamic acid isopropyl ester | 382 (M + 1) |
| 35 | (±)-[7-Cyano-4-(6-methyl-pyrazin-2-ylmethyl)-1,2,3,4-tetrahydro-cyclopenta[b]indol-2-yl]-carbamic acid isopropyl ester | 390 (M + 1) |
| 36 | (±)-(7-Cyano-4-pyrazin-2-ylmethyl-1,2,3,4-tetrahydro-cyclopenta[b]indol-2-yl)-carbamic acid tert-butyl ester | 390.2 (M + 1) |
| 37 | (±)-(7-Cyano-4-isothiazol-3-ylmethyl-1,2,3,4-tetrahydro-cyclopenta[b]indol-2-yl)-carbamic acid tert-butyl ester | 395 (M + 1) |
| 38 | (S)-(7-Cyano-4-isothiazol-3-ylmethyl-1,2,3,4-tetrahydro-cyclopenta[b]indol-2-yl)-carbamic acid isopropyl ester | 381 (M + 1), 425 (M + HCO$_2^-$) |
| 39 | (S)-(7-Cyano-4-thiazol-2-ylmethyl-1,2,3,4-tetrahydro-cyclopenta[b]indol-2-yl)-carbamic acid isopropyl ester | 381 (M + 1), 425 (M + HCO$_2^-$) |
| 40 | (S)-(7-Cyano-4-[1,2,5]thiadiazol-3-ylmethyl-1,2,3,4-tetrahydro-cyclopenta[b]indol-2-yl)-carbamic acid isopropyl ester | 382 (M + 1), 426 (M + HCO$_2^-$) |
| 41 | (R)-(7-Cyano-4-isothiazol-3-ylmethyl-1,2,3,4-tetrahydro-cyclopenta[b]indol-2-yl)-carbamic acid tert-butyl ester | 395 (M + 1) |
| 42 | (S)-(7-Cyano-4-isothiazol-3-ylmethyl-1,2,3,4-tetrahydro-cyclopenta[b]indol-2-yl)-carbamic acid tert-butyl ester | 395 (M + 1) |
| 43** | (S)-(7-Cyano-4-isothiazol-3-ylmethyl-1,2,3,4-tetrahydro-cyclopenta[b]indol-2-yl)-carbamic acid ethyl ester | 367 (M + 1) |
| 44 | (S)-(7-Cyano-4-thiazol-5-ylmethyl-1,2,3,4-tetrahydro-cyclopenta[b]indol-2-yl)-carbamic acid isopropyl ester | 381 (M + 1), 425 (M + HCO$_2^-$) |
| 45 | (S)-[4-(5-Bromo-isothiazol-3-ylmethyl)-7-cyano-1,2,3,4-tetrahydro-cyclopenta[b]indol-2-yl]-carbamic acid isopropyl ester | 459, 461 (M + 1) |
| 46 | (R)-[4-(6-Fluoro-pyridin-2-ylmethyl)-7-(methoxyimino-methyl)-1,2,3,4-tetrahydro-cyclopenta[b]indol-2-yl]-carbamic acid tert-butyl ester | 439 (M + 1) |
| 47 | (S)-[4-(3-Chloro-pyrazin-2-ylmethyl)-7-cyano-1,2,3,4-tetrahydro-cyclopenta[b]indol-2-yl]-carbamic acid isopropyl ester | 410 (M + 1), 408 (M − 1) |
| 48** | (S)-(7-Cyano-4-[1,2,5]thiadiazol-3-ylmethyl-1,2,3,4-tetrahydro-cyclopenta[b]indol-2-yl)-carbamic acid ethyl ester | 403 (M + 1) |
| 49 | (±)-Cyclopropanecarboxylic acid [7-cyano-4-(6-fluoro-pyridin-2-ylmethyl)-1,2,3,4-tetrahydro-cyclopenta[b]indol-2-yl]-amide | 375 (M + 1) |
| 50 | (±)-N-(7-Cyano-4-pyridin-2-ylmethyl-1,2,3,4-tetrahydro-cyclopenta[b]indol-2-yl)-isobutyramide | 359 (M + 1) |
| 51 | (±)-N-[4-(6-Fluoro-pyridin-2-ylmethyl)-7-(methoxyimino-methyl)-1,2,3,4-tetrahydro-cyclopenta[b]indol-2-yl]-isobutyramide | 409 (M + 1) |
| 52 | (R)-Cyclopropanecarboxylic acid [7-cyano-4-(6-fluoro-pyridin-2-ylmethyl)-1,2,3,4-tetrahydro-cyclopenta[b]indol-2-yl]-amide | 375 (M + 1), 419 (M + HCO$_2^-$) |
| 53 | (S)-Cyclopropanecarboxylic acid [7-cyano-4-(6-fluoro-pyridin-2-ylmethyl)-1,2,3,4-tetrahydro-cyclopenta[b]indol-2-yl]-amide | 375 (M + 1), 419 (M + HCO$_2^-$) |
| Intermediate 40 | (S)-{7-Cyano-4-[2-(1,3-dioxo-1,3-dihydro-isoindol-2-yl)-pyridin-3-ylmethyl]-1,2,3,4-tetrahydro-cyclopenta[b]indol-2-yl}-carbamic acid isopropyl ester | 520 (M + 1) |
| Intermediate 41*** | 5-((S)-7-Cyano-2-isopropoxycarbonylamino-2,3-dihydro-1H-cyclopenta[b]indol-4-ylmethyl)-thiazole-4-carboxylic acid ethyl ester | LC-ES/MS m/z 453 (M + 1), 451 (M − 1), T$_R$ = 2.4 min |

*2-Bromomethyl-3-hydroxypyridine hydrobromide is commercially available from Lancaster Synthesis.
**Obtain the example shown by chiral separation of racemic product, according to the procedure generally outlined for Example 1a, 1b.
***Run reaction at room temperature.

Alternate Procedure for Intermediate 40

{(S)-7-Cyano-4-[2-(1,3-dioxo-1,3-dihydro-isoindol-2-yl)-pyridin-3-ylmethyl]-1,2,3,4-tetrahydro-cyclopenta[b]indol-2-yl}-carbamic acid isopropyl ester

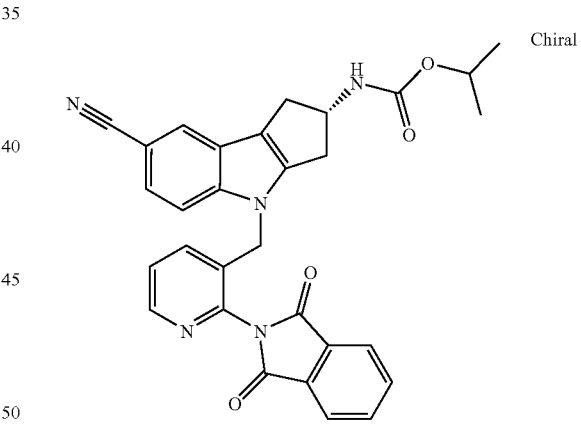

Dissolve (S)-(7-cyano-1,2,3,4-tetrahydro-cyclopenta[b]indol-2-yl)-carbamic acid isopropyl ester (20 g, 70.59 mmoles; ee>98%, 2$^{nd}$ isomer on Chiracel OJ, 0.2% DMEA in Hexane/EtOH [80:20]) in dimethyl sulfoxide (160 mL) and add 2-(3-bromomethyl-pyridin-2-yl)-isoindole-1,3-dione (29.8 g, 84.71 mmol). Stir the mixture until a clear solution is obtained. Add cesium carbonate (46.4 g, 141.18 mmoles) and dimethylaminopyridine (875.5 mg, 7.06 mmol) in one portion. Stir the resulting mixture at 22/24° C. for 2 h. Add the mixture onto water (1.4 L). Stir the resulting suspension for 30 min and filter. Wash the resulting cake with water (100 ml). Dissolve the isolated wet solid in dichloromethane (750 mL) and separate the organic layer. Wash the organic layer with brine and evaporate the organic solvent. Purify the resulting material by silica gel chromatography, eluting with hexanes/acetone/CH$_2$Cl$_2$ (3/1/1) to obtain 24 g (58%). MS (m/z): 520 (M+1).

Example 54

(S)-[4-(2-Amino-pyridin-3-ylmethyl)-7-cyano-1,2,3,4-tetrahydro-cyclopenta[b]indol-2-yl]-carbamic acid isopropyl ester

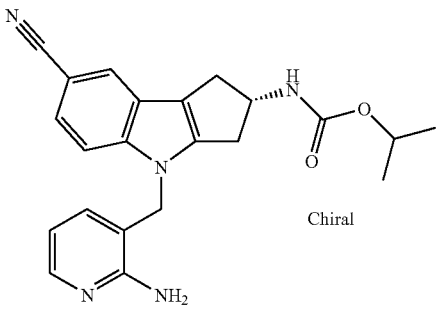

Chiral

Combine crude (S)-{7-cyano-4-[2-(1,3-dioxo-1,3-dihydro-isoindol-2-yl)-pyridin-3-ylmethyl]-1,2,3,4-tetrahydro-cyclopenta[b]indol-2-yl}-carbamic acid isopropyl ester (2.12 mmol, 1100 mg crude material) in a mixture of THF (22 mL) and ethanol (4 mL) and stir for 15 min. Add hydrazine hydrate 0.5 mL, 10 mmol) and stir the mixture at room temperature for 18 h. Vacuum filter the crude reaction and wash the solid with THF (50 mL). Collect the filtrate and remove the solvent under vacuum. Purify the resulting residue by silica gel chromatography (50-100% ethyl acetate/CH$_2$Cl$_2$) to provide 110 mg (13%) of the title compound. MS (m/z): 390 (M+1).

Alternate procedure: Dissolve (S)-{7-cyano-4-[2-(1,3-dioxo-1,3-dihydro-isoindol-2-yl)-pyridin-3-ylmethyl]-1,2,3,4-tetrahydro-cyclopenta[b]indol-2-yl}-carbamic acid isopropyl ester (20 g; 34.64 mmoles) in tetrahydrofuran (170 mL) and ethanol (30 mL). Add hydrazine monohydrate (3.37 mL, 69.29 mmoles) using a syringe pump over 30 min. Stir the mixture at 22/24° C. for 3 h and then filter. Wash the cake with additional tetrahydrofuran (50 ml). Evaporate the combined mother liquors and purify the resulting residue by silica gel chromatography eluting with dichloromethane/(2M NH$_3$ in methanol/) (98:2). Combine the fractions containing pure product and evaporate the solvent. Dry the solid to constant weight and then add over ethanol (50 mL). Heat the mixture to reflux until complete dissolution occurs and then allow to cool to room temperature overnight. Filter the solid and dry under vacuum to constant weight to provide 11.45 g (84%) of the title compound. MS (m/z): 390 (M+1). Chiral HPLC: ee>98% (Isomer 1, Chiralpak AD, EtOH/0.2% dimethylethylamine)

Intermediate 42

(±)-2-(1,3-Dioxo-1,3-dihydro-isoindol-2-yl)-4-(6-fluoro-pyridin-2-ylmethyl)-1,2,3,4-tetrahydro-cyclopenta[b]indole-7-carbonitrile

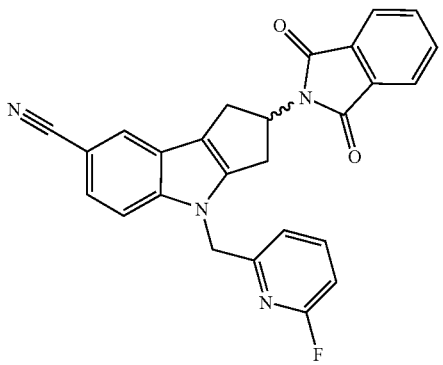

Dissolve (±)-2-(1,3-dioxo-1,3-dihydro-isoindol-2-yl)-1,2,3,4-tetrahydro-cyclopenta[b]indole-7-carbonitrile (6.88 g, 21.0 mmol) and 2-bromomethyl-6-fluoro-pyridine (3.99 g, 21.0 mmol) in DMF (80 mL). Add cesium carbonate (7.51 g, 23.1 mmol, 1.10 equivalents) and stir the reaction mixture at room temperature under nitrogen for 48 h. Dilute the reaction with ethyl acetate, wash with water (3×), dry over anhydrous sodium sulfate, filter, and concentrate to obtain a semi-solid (8.10 g). Purify the crude product on a 120 g silica gel column eluting with 0 to 100% ethyl acetate/hexanes to obtain 6.7 g of a tan/brown solid. Suspend the product in ether (100 mL) at room temperature overnight. Filter the solid, rinse with ether, and dry under high vacuum to obtain the title compound as a tan solid (5.70 g, 62%). LCMS 437.1 (M+1).

Intermediate 43

(±)-2-(1,3-Dioxo-1,3-dihydro-isoindol-2-yl)-4-pyridin-2-ylmethyl-1,2,3,4-tetrahydro-cyclopenta[b]indole-7-carbonitrile

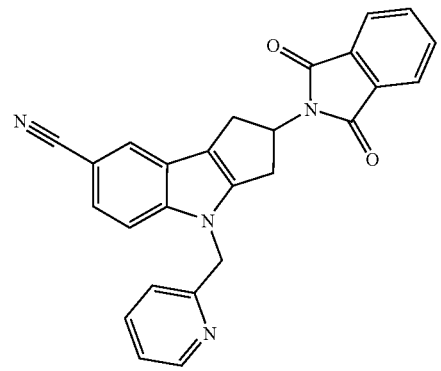

Heat a mixture of 2-(1,3-dioxo-1,3-dihydro-isoindol-2-yl)-1,2,3,4-tetrahydro-cyclopenta[b]indole-7-carbonitrile (5 g, 15.3 mmol) in DMF (25 ml) to 40° C. Add cesium carbonate (10.4 g, 32.4 mmol) and 2-bromomethylpyridine hydrobromide (4.05 g, 16 mmol). Stir the mixture at 40° C. for 24 h. Add the mixture to water (250 mL) and stir for 1 h. Filter the solids and dry the collected material under vacuum. Add the solid to ethanol (25 mL) and reflux for 30 min. Cool the mixture to 22° C. and filter. Dry the solid under vacuum to constant weight to provide 4.8 g (75%) of the title compound. MS (m/z): 419 (M+1).

Intermediate 44

(±)-2-Amino-4-(6-fluoro-pyridin-2-ylmethyl)-1,2,3,4-tetrahydro-cyclopenta[b]indole-7-carbonitrile

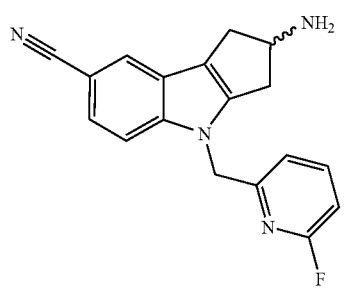

Dissolve (±)-2-(1,3-dioxo-1,3-dihydro-isoindol-2-yl)-4-(6-fluoro-pyridin-2-ylmethyl)-1,2,3,4-tetrahydro-cyclopenta[b]indole-7-carbonitrile (5.31 g, 12.2 mmol) in ethanol (15 mL)/tetrahydrofuran (85 mL). Add hydrazine monohydrate (4.43 ml, 91.2 mmol, 7.50 equivalents) and stir at room temperature under nitrogen overnight. Dilute with ethyl acetate (150 ml), filter off white solids, wash the organic layer with 10% potassium carbonate twice, dry over anhydrous sodium sulfate, filter, and concentrate to obtain the title compound as an orange oil (3.42 g, 91%). LCMS 307.0 (M+1), 305.0 (M−1).

Intermediate 45

(±)-2-Amino-4-pyridin-2-ylmethyl-1,2,3,4-tetrahydro-cyclopenta[b]indole-7-carbonitrile hydrochloride

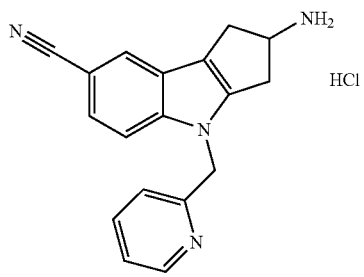

Add 2-(1,3-dioxo-1,3-dihydro-isoindol-2-yl)-4-pyridin-2-ylmethyl-1,2,3,4-tetrahydro-cyclopenta[b]indole-7-carbonitrile (77 g, 184 mmol) to THF (1.3 L) and ethanol (230 mL). Stir the mixture for 10 min and then add hydrazine monohydrate (20 mL, 400 mmol). Stir the mixture at 22° C. for 16 h. Filter the mixture and evaporate the mother liquors. Dissolve the residue in dichloromethane (300 mL). Add a solution of 4M hydrogen chloride in dioxane (50 mL) and stir the mixture for 2 h. Filter and dry the isolated solid under vacuum to constant weight to provide 54 g (90%) of the title compound. MS (m/z): 289 (M+1).

Prepare the following chiral carbamic acid tert-butyl esters, Intermediates 46-51 in Table 3, using Intermediate 16 and alkylating with the appropriate heteroarylmethyl halide or heteroarylmethyl mesylate, essentially as described in the procedures of Example 1 and Example 2.

TABLE 3

| Intermediate | Chemical Name | MS (m/z) |
|---|---|---|
| 46 | (R)-(7-Cyano-4-[1,2,5]thiadiazol-3-ylmethyl-1,2,3,4-tetrahydro-cyclopenta[b]indol-2-yl)-carbamic acid tert-butyl ester | 396 (M + 1) |
| 47 | (R)-(7-Cyano-4-thiazol-4-ylmethyl-1,2,3,4-tetrahydro-cyclopenta[b]indol-2-yl)-carbamic acid tert-butyl ester | 395 (M + 1) |
| 48 | (R)-(7-Cyano-4-thiazol-2-ylmethyl-1,2,3,4-tetrahydro-cyclopenta[b]indol-2-yl)-carbamic acid tert-butyl ester | 395 (M + 1) |
| 49 | (R)-(7-Cyano-4-thiazol-5-ylmethyl-1,2,3,4-tetrahydro-cyclopenta[b]indol-2-yl)-carbamic acid tert-butyl ester | 395 (M + 1) |
| 50 | (R)-{7-Cyano-4-[2-(1,3-dioxo-1,3-dihydro-isoindol-2-yl)-pyridin-3-ylmethyl]-1,2,3,4-tetrahydro-cyclopenta[b]indol-2-yl}-carbamic acid tert-butyl ester | 534 (M + 1) |
| 51 | (R)-5-(2-tert-Butoxycarbonylamino-7-cyano-2,3-dihydro-1H-cyclopenta[b]indol-4-ylmethyl)-thiazole-4-carboxylic acid ethyl ester | 467 (M + 1) |

Intermediate 52

(R)-2-Amino-4-isothiazol-3-ylmethyl-1,2,3,4-tetrahydro-cyclopenta[b]indole-7-carbonitrile dihydrochloride

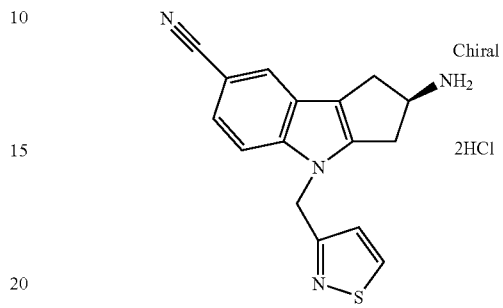

Stir a suspension of (R)-(7-cyano-4-isothiazol-3-ylmethyl-1,2,3,4-tetrahydro-cyclopenta[b]indol-2-yl)-carbamic acid tert-butyl ester (1.16 g, 3.19 mmol) in 4M HCl in dioxane (20 mL) for 2 h at room temperature, then concentrate in vacuo. Dry the residue under vacuum overnight at 40° C. MS (m/z): 295 (M+1).

Prepare the following amines, Intermediates 53-59 listed in Table 4, essentially as described in the procedure for Intermediate 52, using the appropriate (7-cyano-4-hetero-arylmethyl-1,2,3,4-tetrahydro-cyclopenta[b]indol-2-yl)-carbamic acid tert-butyl ester. Isolate the amines as hydrochloride or dihydrochloride salts.

TABLE 4

| Intermediate | Chemical name | MS (m/z) |
|---|---|---|
| 53 | (±)-2-Amino-4-pyrazin-2-ylmethyl-1,2,3,4-tetrahydro-cyclopenta[b]indole-7-carbonitrile | 290 (M + 1) |
| 54 | (R)-2-Amino-4-[1,2,5]thiadiazol-3-ylmethyl-1,2,3,4-tetrahydro-cyclopenta[b]indole-7-carbonitrile | 296 (M + 1) |
| 55 | (R)-2-Amino-4-thiazol-4-ylmethyl-1,2,3,4-tetrahydro-cyclopenta[b]indole-7-carbonitrile | 295 (M + 1) |
| 56 | (R)-2-Amino-4-thiazol-2-ylmethyl-1,2,3,4-tetrahydro-cyclopenta[b]indole-7-carbonitrile | 295 (M + 1) |
| 57 | (R)-2-Amino-4-thiazol-5-ylmethyl-1,2,3,4-tetrahydro-cyclopenta[b]indole-7-carbonitrile | No data |
| 58 | (R)-2-Amino-4-[2-(1,3-dioxo-1,3-dihydro-isoindol-2-yl)-pyridin-3-ylmethyl]-1,2,3,4-tetrahydro-cyclopenta[b]indole-7-carbonitrile | 434 (M + 1) |
| 59 | (R)-5-(2-Amino-7-cyano-2,3-dihdro-1H-cyclopenta[b]indol-4-ylmethyl)-thiazole-4-carboxylic acid ethyl ester | 367 (M + 1) |

Example 55

(±)-3-[7-Cyano-4-(6-fluoro-pyridin-2-ylmethyl)-1,2,3,4-tetrahydro-cyclopenta[b]indol-2-yl]-1,1-dimethyl-urea

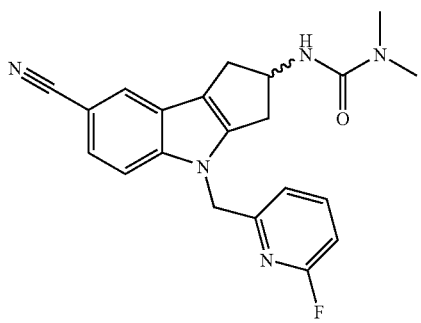

To a solution of (±)-2-amino-4-(6-fluoro-pyridin-2-ylmethyl)-1,2,3,4-tetrahydro-cyclopenta[b]indole-7-carbonitrile (70 mg, 0.23 mmol) and diisopropylethylamine (0.35 mmol, 61 µL) in dichloromethane (1 mL) add N,N-dimethylcarbamoyl chloride (0.35 mmol, 32 µL) and stir at room temperature overnight. Load the solution on silica gel and purify by column chromatography (0-100% ethyl acetate/dichloromethane) to obtain the title compound. LCMS 378.1 (M+1).

Example 56

(±)-(7-Cyano-4-pyridin-2-ylmethyl-1,2,3,4-tetrahydro-cyclopenta[b]indol-2-yl)-carbamic acid isopropyl ester

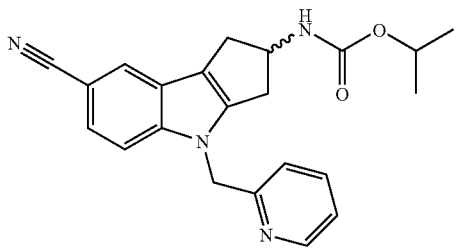

To a solution of (±)-2-amino-4-pyridin-2-ylmethyl-1,2,3,4-tetrahydro-cyclopenta[b]indole-7-carbonitrile (2.32 g, 8.05 mmol) and diisopropylethylamine (9.65 mmol, 1.68 mL) in dichloromethane (10 mL) add isopropylchloroformate (8.86 mmol, 8.9 mL) and stir at room temperature overnight. Dilute with ethyl acetate and wash with 10% K$_2$CO$_3$ solution (2×). Dry the organic portion over Na$_2$SO$_4$, filter, and concentrate to obtain 3.3 g. Purify by column chromatography (0-100% ethyl acetate/dichloromethane) to obtain 2.48 g (82%) of the racemic product. LCMS 375.2 (M+1).

Alternate Procedure:

Add (±)-2-amino-4-pyridin-2-ylmethyl-1,2,3,4-tetrahydro-cyclopenta[b]indole-7-carbonitrile hydrochloride (35 g, 108 mmol) to a mixture of dichloromethane (350 mL) and pyridine (70 mL). Stir the mixture under nitrogen and cool to 5° C. Add isopropyl chloroformate (1M solution in toluene, 162 mL, 162 mmol). Remove the ice bath and stir the mixture at 22° C. After 16 h evaporate the solvent. Add the resulting residue to water (350 mL) and stir 2 h. Filter and dry the collected solid under vacuum at 45° C. Add the solid to ethyl acetate (400 mL) and heat the mixture to reflux. Then cool to 22° C. and filter the solid. Add the wet solid to ethyl acetate (200 mL) and heat to reflux for 30 min. Cool the mixture to 22° C. over one hour and then cool to 0-5° C. during 5 min. Filter the mixture and dry the isolated solid under vacuum to constant weight to provide 23 g (62%) of the title compound. MS (m/z): 374 (M+1).

Example 56a & 56b (R)- and (S)-(7-Cyano-4-pyridin-2-ylmethyl-1,2,3,4-tetrahydro-cyclopenta[b]indol-2-yl)-carbamic acid isopropyl ester Separate enantiomers of Example 56 by preparative chiral chromatography using Chiralpak AD column (8×33 cm), eluting with 100% EtOH at 375 mL/min and 250 nm. Isomer 1 (R): 1.14 g, 99.9% ee (analytical conditions: Chiralpak AD-H column, eluting with 100% EtOH/0.2% dimethylethylamine; LCMS 375.2 (M+1). Isomer 2 (S): 1.67 g, 99.4% ee; LCMS 375.2 (M+1).

First alternate route to 56(b): (S)-(7-Cyano-4-pyridin-2-ylmethyl-1,2,3,4-tetrahydro-cyclopenta[b]indol-2-yl)-carbamic acid isopropyl ester

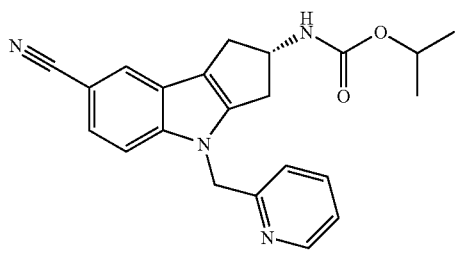

Add (S)-7-cyano-1,2,3,4-tetrahydro-cyclopenta[b]indol-2-yl)-carbamic acid isopropyl ester (Intermediate 15) (13 g, 41.3 mmol) to DMF (100 mL) and warm the solution to 40° C. Add cesium carbonate (42 g, 129 mmol) in one portion and stir the mixture for 30 min at 40° C. Add 2-bromomethylpyridine hydrobromide 21 g, 83 mmol) portionwise over 4 h. Stir the mixture at 40° C. for 18 h. Add the mixture to chilled water (1 L) at 0 to 5° C. and stir for 30 min. Isolate the solid by filtration and dry under vacuum to constant weight. Pass the material over a silica gel pad eluting with CH$_2$Cl$_2$/EtOAc (7/3). Combine the fractions containing the product and evaporate the solvent to give a pale brown solid. Recrystallize from ethyl acetate to give 15.3 g (77%) of the title compounds. LC/MS (m/z) 375 (M+1).

Second Alternate Route to 56b:

(HPLC conditions—column: Zorbax® SB-Phenyl, Rapid Resolution, 4.6×75 mm, 3.5 micron; solvent: 10% acetonitrile/90% water with 0.05% TFA; UV at 230 nm)

Step 1: (±)-(7-Cyano-1,2,3,4-tetrahydro-cyclopenta[b]indol-2-yl)-carbamic acid tert-butyl ester Equip a 12 L 3-necked round bottom flask with overhead agitation, thermocouple, addition funnel, nitrogen inlet, and cooling bath. Charge the flask with (±)-2-(1,3-dioxo-1,3-dihydro-isoindol-2-yl)-1,2,3,4-tetrahydro-cyclopenta[b]indole-7-carbonitrile (500 g, 1.53 moles) and THF (5 L). Stir the resulting slurry at ambient temperature. Add hydrazine monohydrate (185.6 mL, 3.82 moles) in a slow stream from an addition funnel over 10 minutes. Stir the resulting mixture at ambient temperature overnight (about 18 h). Add cool water to the bath and charge the addition funnel with di-t-butyl dicarbonate (875.1 g, 4.01 moles; previously melted to a liquid). Add to the reaction mixture over 2 hours, keeping the pot temperature below 30° C. After 15 min, analyze by HPLC to find complete consumption of the intermediate amine Filter the reaction mixture onto a polypropylene pad in a stainless steel, table-top filter, and wash the resulting filter cake with ethyl acetate (2×1 L). Concentrate the filtrate in vacuo to remove most of the THF. Purify the resulting mixture (about 1 L) over a plug of silica gel (4 Kg Kieselgel-60), eluting with ethyl acetate. Concentrate the recovered eluent in vacuo to a dark oil. Add heptane (2 L) and ethyl acetate (350 mL) and spin the contents on a rotary evaporator at ambient temperature for 2 h. Add ice to the bath and spin the resulting slurry at 5° C. for an additional 2 h. Filter the solids, rinse with 90/10 heptane/ethyl acetate (2×500 mL) and vacuum dry at 35° C. Obtain the titled compound as a light tan solid in 91.6% yield.

Step 2: (±)-(7-Cyano-4-pyridin-2-ylmethyl-1,2,3,4-tetrahydro-cyclopenta[b]indol-2-yl)-carbamic acid tert-butyl ester Equip a 20 L bottom outlet flask with overhead agitation, thermocouple, and nitrogen inlet. Charge the flask with (±)-(7-cyano-1,2,3,4-tetrahydro-cyclopenta[b]indol-2-yl)-carbamic acid tert-butyl ester (500 g, 1.68 moles) and dichloromethane (5 L). Begin agitation and add tetra n-butylammonium hydrogen sulfate (58.9 g, 0.168 mol) followed by 2-(bromomethyl)pyridine hydrobromide (510.4 g, 2.02 moles). Add deionized water (2 L) followed by a 50% NaOH solution (445.3 mL, 8.41 moles). Stir the resulting mixture vigorously overnight (about 21 h). Stop the agitation, allow the layers to separate, and discard the aqueous (upper) layer. Wash the organics with deionized water (3×4 L), dry over sodium sulfate, and concentrate in vacuo to about 500 mL. Purify the crude material over a silica gel plug (7 Kg Keiselgel 60) using 1:1 ethyl acetate/heptane as eluent. Concentrate the eluent in vacuo to afford 560 grams of the titled compound as an off-white solid (81.4%).

Step 3: (R)- and (S)-(7-Cyano-4-pyridin-2-ylmethyl-1,2,3,4-tetrahydro-cyclopenta[b]indol-2-yl)-carbamic acid tert-butyl ester Use the following analytical chiral HPLC method to analyze enantiomers: 4.6×150 mm Chiralpak AD-H column (Chiral Technologies), 20:80:0.2 acetonitrile/3 A grade denatured ethanol/dimethylethylamine mobile phase, 0.6 mL/min flow rate, UV detection @ 255 nm. Enantiomer 1 elutes at 4.0 min. and enantiomer 2 elutes at 5.2 min. An 8% impurity (255 nm) elutes at 3.6 min. Purify (±)-(7-cyano-4-pyridin-2-ylmethyl-1,2,3,4-tetrahydro-cyclopenta[b]indol-2-yl)-carbamic acid tert-butyl ester (528 g) by preparative chiral HPLC using the following conditions: 8×33 cm Chiralpak AD column, same mobile phase as analytical, 375 mL/min flow rate, UV detection at 270 nm. Dissolve 108 g of sample in the mobile phase at a final concentration of 75 mg/mL final. Load 4.0 g/injection with the enantiomer 1 fraction eluting between 3.5-5.5 min. and enantiomer 2 eluting between 6-10 min. Set the final run time at 7.5 min/injection with partial stacking of the enantiomer 2 profile eluting just after each injection to reduce solvent consumption. Purify the remaining 420 g over a plug of silica using Merck 9385 60 Angstrom 230-400 mesh silica gel, eluting with a 1:2:7 dichloromethane/heptane/methyl t-butyl ether solvent system. Use a 3.5 kg silica pad with vacuum filtration at 140 g sample/plug. Racemate begins to emerge after 5 column volumes. Use 100% methyl t-butyl ether followed by 100% acetone to push the remaining racemate off the plug. Obtain a total of 358.5 g of 98+% pure racemate in this manner. Resolve this material as above by preparative chiral HPLC. Obtain 208.8 g (99.9% ee) of enantiomer 1 (R isomer) and 197 g (99.6% ee) of enantiomer 2 (S isomer).

Step 4: (S)-2-Amino-4-pyridin-2-ylmethyl-1,2,3,4-tetrahydro-cyclopenta[b]indole-7-carbonitrile hydrochloride Equip a 3 L 3-necked round bottom flask with a heating mantle, air stirrer, temperature probe, nitrogen inlet, and addition funnel Charge the flask with (S)-(7-cyano-4-pyridin-2-ylmethyl-1,2,3,4-tetrahydro-cyclopenta[b]indol-2-yl)-carbamic acid tert-butyl ester (85.0 g, 0.22 moles), and EtOH (850 mL). Add concentrated HCl (180 mL, 2.20 moles) in one portion. Heat the resulting solution to 45-50° C. and stir for 90 min, after which analyze by HPLC to indicate complete consumption of starting material. Transfer the mixture to a Buchi flask, dilute with deionized water (595 mL), and concentrate in vacuo to remove EtOH. Add EtOAc in two portions (2×170 mL) and re-strip to remove both the EtOAc and residual EtOH. Transfer the aqueous concentrate to a 5 L reaction flask, and cool to 10-15° C. While maintaining the temperature of the reaction at <30° C., adjust the pH of the solution to 11-12 by the drop-wise addition of 5 M NaOH (950 mL). Extract the resulting mixture with $CH_2Cl_2$ (1300 mL, 800 mL). Wash the combined $CH_2Cl_2$ extracts with deionized water (500 mL), dry over $Na_2SO_4$, and concentrate in vacuo to afford titled compound as a light green solid (65.0 g, 103%).

Step 5: (S)-(7-Cyano-4-pyridin-2-ylmethyl-1,2,3,4-tetrahydro-cyclopenta[b]indol-2-yl)-carbamic acid isopropyl ester

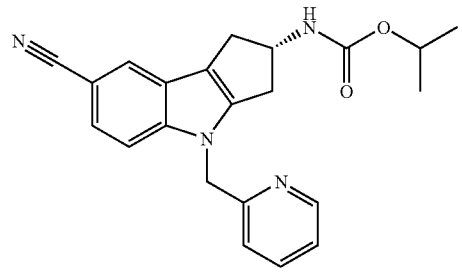

Equip a 2 L reaction flask with a cooling bath, air stirrer, temperature probe, and addition funnel Charge the flask with (S)-2-amino-4-pyridin-2-ylmethyl-1,2,3,4-tetrahydro-cyclopenta[b]indole-7-carbonitrile hydrochloride (62.8 g, 0.218 moles), DMF (188 mL), and triethylamine (33.4 mL, 0.240 mol). Cool the resulting solution to 0° C. using an ice/acetone bath. While maintaining the temp at <10° C., add isopropyl chloroformate (218 mL, 0.218 mol, 1 M in toluene) drop-wise via an addition funnel. When the addition is complete, remove the cooling bath was removed and allow the mixture to warm to ambient temperature. After 1 hour, analyze by HPLC to indicate the reaction is complete, and pour the mixture into a solution of deionized water (1256 mL) and EtOAc (1884 mL). Separate the layers, filter the organic layer, and re-wash with a 1:1 water:brine solution, then dry over $Na_2SO_4$. Concentrate in vacuo at 55° C. to about 15 volumes, and allow the resulting to cool to ambient temperature, affording a white precipitate. Add heptane (628 mL) and stir for 20 min. Concentrate the mixture back to about 15 volumes. Filter the solids, wash with heptane, and dry to give the titled compound as a fluffy white solid (68.9 g, 84.5%). $^1$H NMR (500 MHz, DMSO-$d_6$), δ 8.49 (dd, 1H), 7.86 (d, 1H, J=1.5), 7.71-

7.75 (m, 1H), 7.60 (d, 1H, J=9.0), 7.57 (d, 1H, J=9.0), 7.36 (dd, 1H), 7.28-7.26 (m, 1H), 7.14 (d, 1H, J=7.5), 5.44 (s, 2H), 4.79-4.72 (m, 1H), 4.71-4.66 (m, 1H), 3.22-3.20 (m, 1H), 3.16-3.12 (m, 1H), 2.73-2.66 (m, 2H), 1.16 (dd, 6H).

Example 57

(R)—N'-[7-Cyano-4-(isothiazol-3-ylmethyl)-1,2,3,4-tetrahydro-cyclopenta[b]indol-2-yl]-N,N-dimethylsulfamide

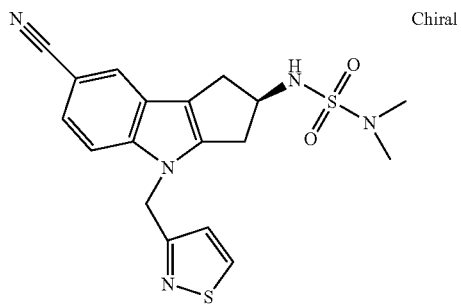

Chiral

Mix (R)-2-amino-4-isothiazol-3-ylmethyl-1,2,3,4-tetrahydro-cyclopenta[b]indole-7-carbonitrile dihydrochloride salt (1.0 g, 2.72 mmol), triethylamine (0.76 mL, 5.44 mmol), and 1,4-diazabicyclo[2,2,2]octane (0.52 g, 4.63 mmol) in $CHCl_3$ (80 mL) and heat in an oil bath until the internal temperature reaches to 54° C. Add a solution of dimethylsulfamoyl chloride (0.35 mL, 3.26 mmol) in $CHCl_3$ (10 mL) drop wise to the reaction mixture via addition funnel under a nitrogen atmosphere over 30 min. Stir the resulting mixture for an additional hour at 54° C. and then cool to room temperature. Dilute with $CH_2Cl_2$ (150 mL), wash the organic layer with saturated $NaHCO_3$, dry ($Na_2SO_4$), filter, and concentrate in vacuo. Purify using silica gel chromatography on with EtOAc/hexane (8/2) to yield 0.82 g (75%) of the title compound. $^1$H NMR (400 MHz, DMSO-$d_6$) δ 9.03 (s, 1H), 7.88 (s, 1H), 7.74 (d, J=5.0 Hz, 1H), 7.64 (d, J=5.1 Hz, 1H), 7.38 (d, J=5.0 Hz, 1H), 7.17 (s, 1H), 5.52 (s, 2H), 4.52-4.40 (m, 2H), 3.31-3.18 (m, 2H), 2.62 (s, 6H).

Using the appropriate racemic or chiral 4-(heteroarylmethyl)-1,2,3,4-tetrahydro-cyclopenta[b]indol-2-ylamine, prepare Examples 58-89 and Intermediates 60-61 in Table 5, using the appropriate chloroformate or acid chloride (essentially according to the procedure described in Example 56) or the appropriate sulfonyl or sulfamoyl chloride (essentially according to the procedure described in Example 57).

TABLE 5

| Example | Chemical Name | Structure | MS (m/z) |
|---|---|---|---|
| 58 | (±)-[7-Cyano-4-(6-fluoro-pyridin-2-ylmethyl)-1,2,3,4-tetrahydro-cyclopenta[b]indol-2-yl]-carbamic acid isopropyl ester | 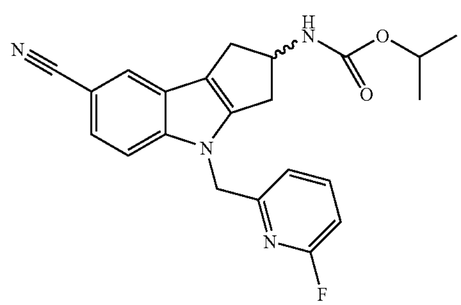 | 393 (M + 1) |
| 59 | (±)-[7-Cyano-4-(6-fluoro-pyridin-2-ylmethyl)-1,2,3,4-tetrahydro-cyclopenta[b]indol-2-yl]-carbamic acid ethyl ester | 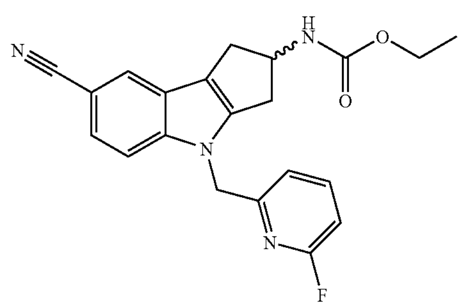 | 379 (M + 1) |
| 60 | (±)-[7-Cyano-4-(6-fluoro-pyridin-2-ylmethyl)-1,2,3,4-tetrahydro-cyclopenta[b]indol-2-yl]-carbamic acid propyl ester | 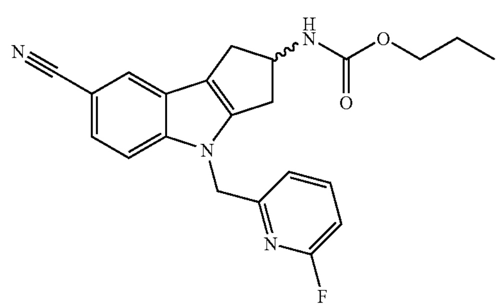 | 393 (M + 1) |

TABLE 5-continued

| Example | Chemical Name | Structure | MS (m/z) |
|---|---|---|---|
| 61 | (±)-(7-Cyano-4-pyridin-2-ylmethyl-1,2,3,4-tetrahydro-cyclopenta[b]indol-2-yl)-carbamic acid ethyl ester | 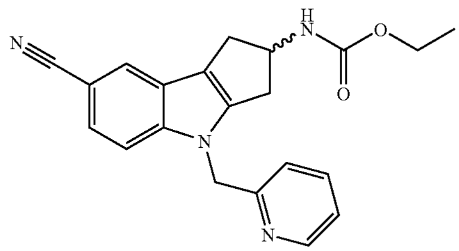 | 361 (M + 1) |
| 62 | (±)-[7-Cyano-4-(6-fluoro-pyridin-2-ylmethyl)-1,2,3,4-tetrahydro-cyclopenta[b]indol-2-yl]-carbamic acid methyl ester | 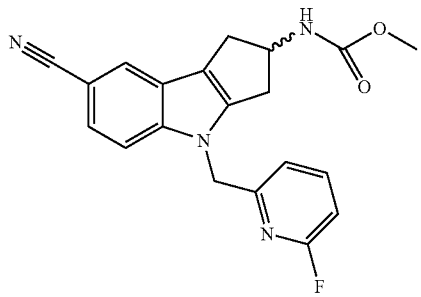 | 365 (M + 1) |
| 63 | (±)-[7-Cyano-4-(6-fluoro-pyridin-2-ylmethyl)-1,2,3,4-tetrahydro-cyclopenta[b]indol-2-yl]-carbamic acid isobutyl ester | 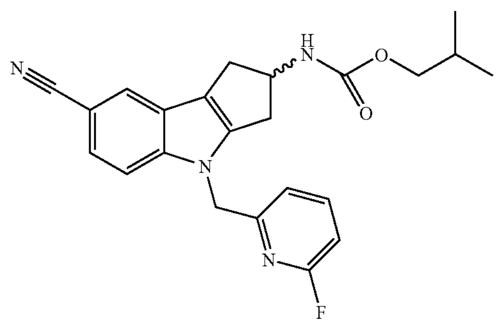 | 407 (M + 1) |
| 64 | (±)-(7-Cyano-4-pyridin-2-ylmethyl-1,2,3,4-tetrahydro-cyclopenta[b]indol-2-yl)-carbamic acid isobutyl ester | 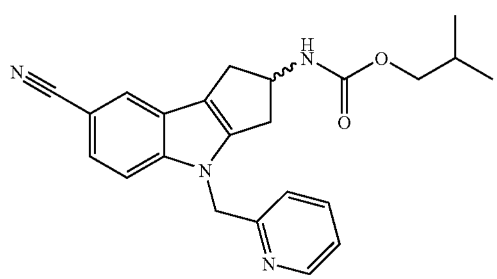 | 389 (M + 1) |
| 65* | (S)-(7-Cyano-4-pyridin-2-ylmethyl-1,2,3,4-tetrahydro-cyclopenta[b]indol-2-yl)-carbamic acid isobutyl ester | 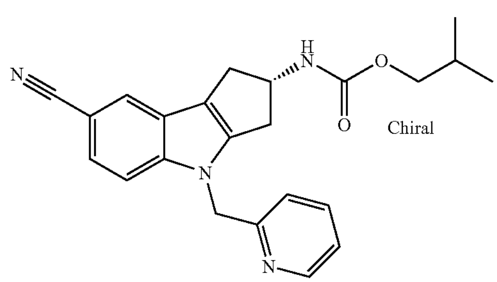 | 389 (M + 1) |

TABLE 5-continued

| Example | Chemical Name | Structure | MS (m/z) |
|---|---|---|---|
| 66* | (R)-(7-Cyano-4-pyridin-2-ylmethyl-1,2,3,4-tetrahydro-cyclopenta[b]indol-2-yl)-carbamic acid isobutyl ester | 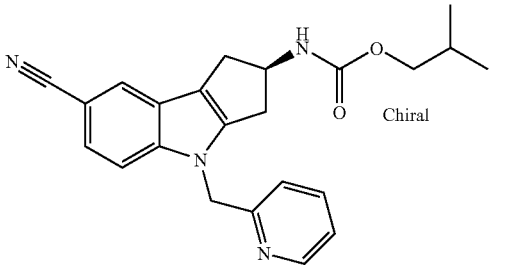 | 389 (M + 1) |
| 67* | (R)-[7-Cyano-4-(6-fluoro-pyridin-2-ylmethyl)-1,2,3,4-tetrahydro-cyclopenta[b]indol-2-yl]-carbamic acid isobutyl ester | 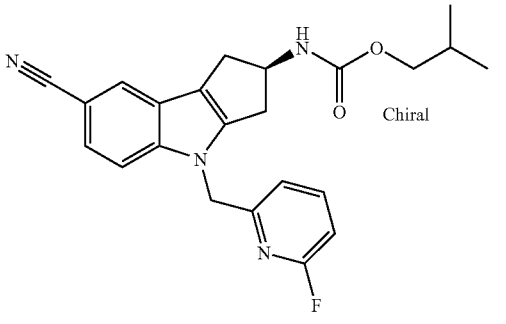 | 407 (M + 1) |
| 68* | (S)-[7-Cyano-4-(6-fluoro-pyridin-2-ylmethyl)-1,2,3,4-tetrahydro-cyclopenta[b]indol-2-yl]-carbamic acid isobutyl ester | 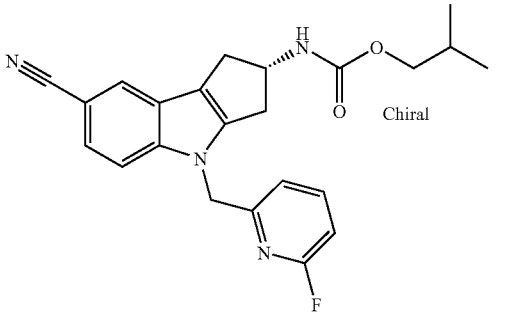 | 407 (M + 1) |
| 69 | (±)-N-[7-Cyano-4-(6-fluoro-pyridin-2-ylmethyl)-1,2,3,4-tetrahydro-cyclopenta[b]indol-2-yl]-methanesulfonamide | 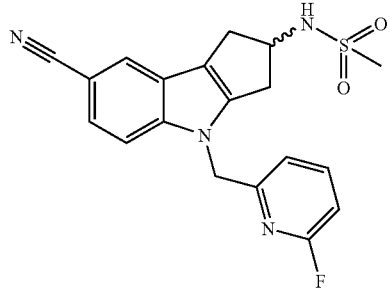 | 385 (M + 1) |
| 70 | (±)-N'-[7-Cyano-4-(6-fluoro-pyridin-2-ylmethyl)-1,2,3,4-tetrahydro-cyclopenta[b]indol-2-yl]-N,N-dimethylsulfamide | 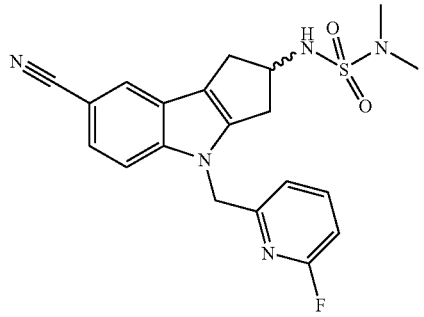 | 414 (M + 1) 412 (M − 1) |

TABLE 5-continued

| Example | Chemical Name | Structure | MS (m/z) |
|---|---|---|---|
| 71 | (±)-Propane-1-sulfonic acid [7-cyano-4-(6-fluoro-pyridin-2-ylmethyl)-1,2,3,4-tetrahydro-cyclopenta[b]indol-2-yl]-amide | 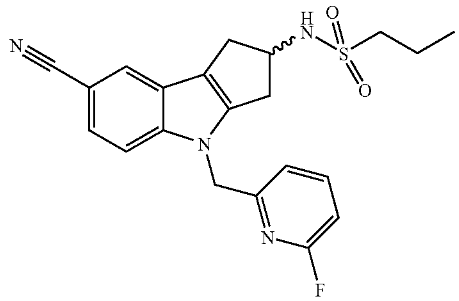 | 413 (M + 1) |
| 72 | (±)-Cyclopropanesulfonic acid [7-cyano-4-(6-fluoro-pyridin-2-ylmethyl)-1,2,3,4-tetrahydro-cyclopenta[b]indol-2-yl]-amide | 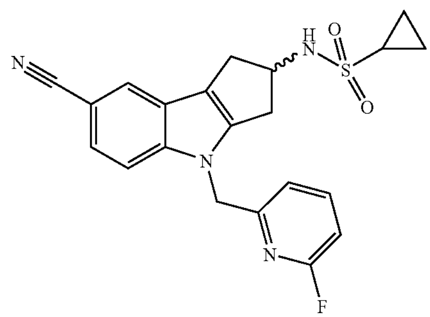 | 411 (M + 1) 409 (M − 1) |
| 73 | (±)-Ethanesulfonic acid [7-cyano-4-(6-fluoro-pyridin-2-ylmethyl)-1,2,3,4-tetrahydro-cyclopenta[b]indol-2-yl]-amide | 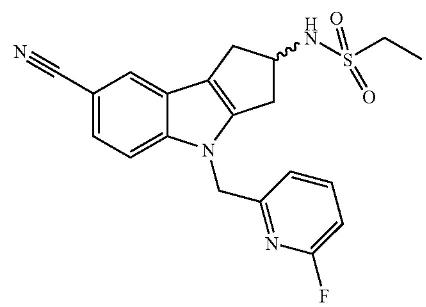 | 399 (M + 1) 397 (M − 1) |
| 74 | (R)-N'-[7-Cyano-4-(6-fluoro-pyridin-2-ylmethyl)-1,2,3,4-tetrahydro-cyclopenta[b]indol-2-yl]-N,N-dimethylsulfamide | Chiral | 414 (M + 1) 412 (M − 1) |
| 75 | (S)-N'-[7-Cyano-4-(6-fluoro-pyridin-2-ylmethyl)-1,2,3,4-tetrahydro-cyclopenta[b]indol-2-yl]-N,N-dimethylsulfamide | Chiral | 414 (M + 1) 412 (M − 1) |

TABLE 5-continued

| Example | Chemical Name | Structure | MS (m/z) |
|---|---|---|---|
| 76 | (±)-N'-[7-Cyano-4-(pyridin-2-ylmethyl)-1,2,3,4-tetrahydro-cyclopenta[b]indol-2-yl]-N,N-dimethylsulfamide | 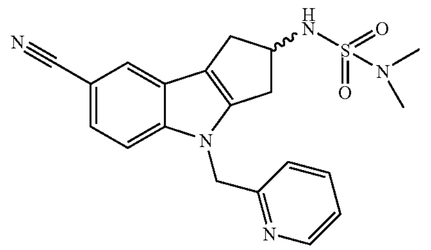 | 396 (M + 1) 394 (M − 1) |
| 77 | (±)-N'-[7-Cyano-4-(6-fluoro-pyridin-2-ylmethyl)-1,2,3,4-tetrahydro-cyclopenta[b]indol-2-yl]-N,N-diethylsulfamide | 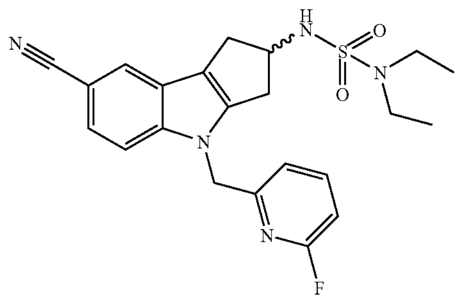 | 442 (M + 1) 440 (M − 1) |
| 78 | (±)-Cyclopropanesulfonic acid (7-cyano-4-pyridin-2-ylmethyl-1,2,3,4-tetrahydro-cyclopenta[b]indol-2-yl)-amide | 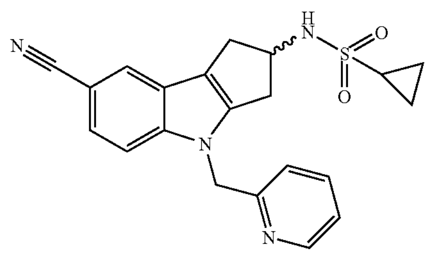 | 393 (M + 1) 391 (M − 1) |
| 79* | (R)-Cyclopropanesulfonic acid [7-cyano-4-(6-fluoro-pyridin-2-ylmethyl)-1,2,3,4-tetrahydro-cyclopenta[b]indol-2-yl]-amide | 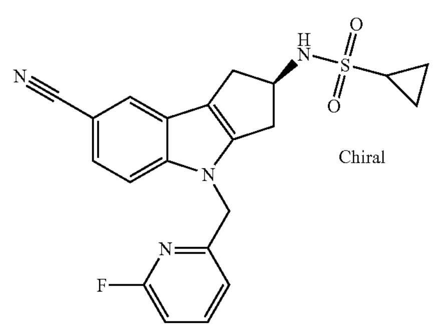 | 411 (M + 1) 409 (M − 1) |
| 80* | (S)-Cyclopropanesulfonic acid [7-cyano-4-(6-fluoro-pyridin-2-ylmethyl)-1,2,3,4-tetrahydro-cyclopenta[b]indol-2-yl]-amide | 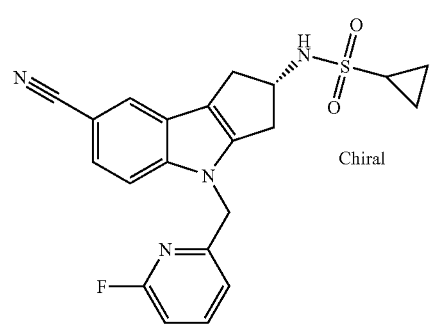 | 411 (M + 1) 409 (M − 1) |

TABLE 5-continued

| Example | Chemical Name | Structure | MS (m/z) |
|---|---|---|---|
| 81 | (±)-N'-[7-Cyano-4-(pyrazin-2-ylmethyl)-1,2,3,4-tetrahydro-cyclopenta[b]indol-2-yl]-N,N-dimethylsulfamide | 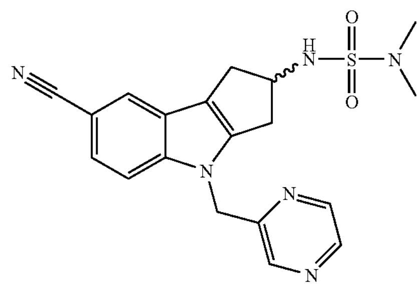 | 397 (M + 1) |
| 82* | (R)-N'-[7-Cyano-4-(pyridin-2-ylmethyl)-1,2,3,4-tetrahydro-cyclopenta[b]indol-2-yl]-N,N-dimethylsulfamide | 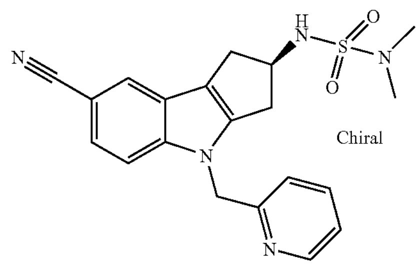 | 396 (M + 1) |
| 83* | (R)-Cyclopropanesulfonic acid (7-cyano-4-pyridin-2-ylmethyl-1,2,3,4-tetrahydro-cyclopenta[b]indol-2-yl)-amide | 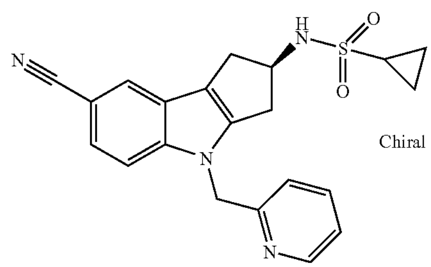 | 393 (M + 1) |
| 84* | (R)-N'-[7-Cyano-4-(pyrazin-2-ylmethyl)-1,2,3,4-tetrahydro-cyclopenta[b]indol-2-yl]-N,N-dimethylsulfamide | 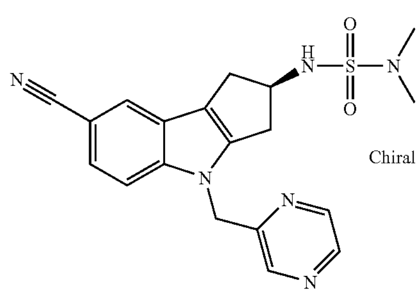 | 397 (M + 1) |
| 85 | (R)-N'-(7-Cyano-4-thiazol-4-ylmethyl-1,2,3,4-tetrahydro-cyclopenta[b]indol-2-yl)-N,N-dimethylsulfamide | 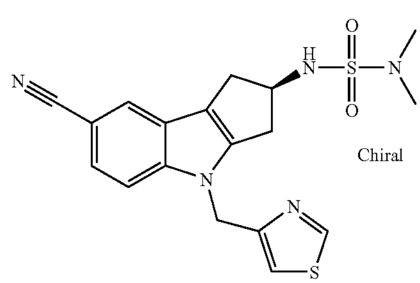 | 402 (M + 1) |

TABLE 5-continued

| Example | Chemical Name | Structure | MS (m/z) |
|---|---|---|---|
| 86 | (R)-N'-(7-Cyano-4-thiazol-2-ylmethyl-1,2,3,4-tetrahydro-cyclopenta[b]indol-2-yl)-N,N-dimethylsulfamide | 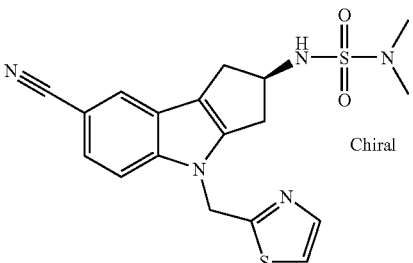 | 402 (M + 1) |
| 87 | (R)-N'-(7-Cyano-4-thiazol-5-ylmethyl-1,2,3,4-tetrahydro-cyclopenta[b]indol-2-yl)-N,N-dimethylsulfamide | 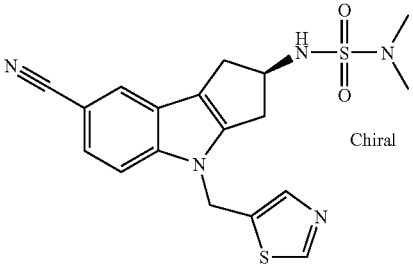 | 402 (M + 1) |
| 88 | (R)-N'-(7-Cyano-4-[1,2,5]thiadiazol-3-ylmethyl-1,2,3,4-tetrahydro-cyclopenta[b]indol-2-yl)-N,N-dimethylsulfamide | 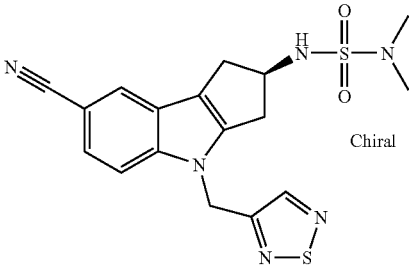 | 403 (M + 1) |
| 89 | (±)-N-[7-Cyano-4-(6-fluoro-pyridin-2-ylmethyl)-1,2,3,4-tetrahydro-cyclopenta[b]indol-2-yl]-propionamide | 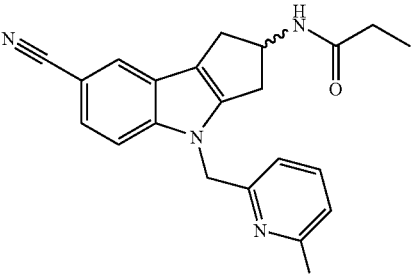 | 363 (M + 1) |
| Intermediate 60 | (R)-N'-{7-Cyano-4-[2-(1,3-dioxo-1,3-dihydro-isoindol-2-yl)-pyridin-3-ylmethyl]-1,2,3,4-tetrahydro-cyclopenta[b]indol-2-yl}-N,N-dimethylsulfamide | 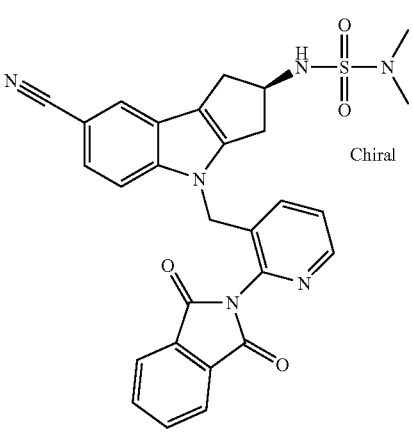 | 541 (M + 1) |

TABLE 5-continued

| Example | Chemical Name | Structure | MS (m/z) |
|---|---|---|---|
| Intermediate 61 | (R)-5-{2-[(dimethylamino)-sulfonyl]-amino-7-cyano-2,3-dihdro-1H-cyclopenta[b]indol-4-ylmethyl}-thiazole-4-carboxylic acid ethyl ester | 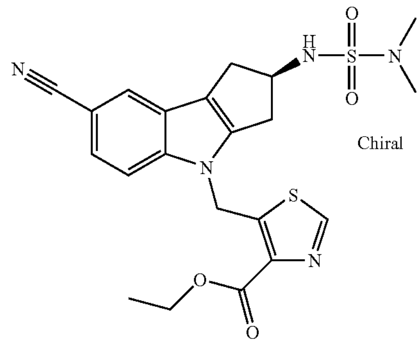 | 474 (M + 1) |

*Obtain the example shown by chiral separation of racemic product, essentially according to the procedure described for Example 56a, 56b.

Example 90

(R)—N'-[4-(2-Amino-pyridin-3-ylmethyl)-7-cyano-1,2,3,4-tetrahydro-cyclopenta[b]indol-2-yl]-N,N-dimethylsulfamide

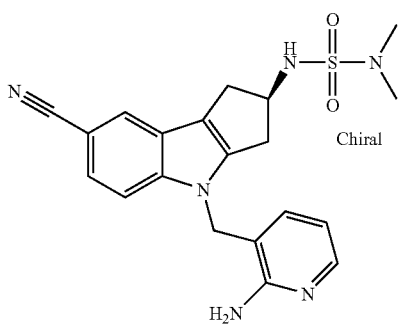

Prepare the title compound essentially using the procedure as described in Example 54, using (R)—N'-{7-cyano-4-[2-(1,3-dioxo-1,3-dihydro-isoindol-2-yl)-pyridin-3-ylmethyl]-1,2,3,4-tetrahydro-cyclopenta[b]indol-2-yl)-N,N-dimethyl-sulfamide to obtain 0.13 g (61%) of product. MS (m/z): 411.0 (M+1).

Intermediate 62

5-((S)-7-Cyano-2-isopropoxycarbonylamino-2,3-dihydro-1H-cyclopenta[b]indol-4-ylmethyl)-thiazole-4-carboxylic acid

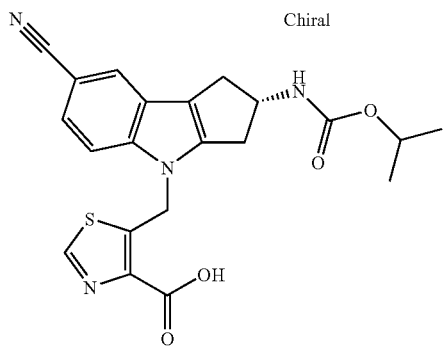

Treat a mixture of 5-((S)-7-cyano-2-isopropoxycarbonylamino-2,3-dihydro-1H-cyclopenta[b]indol-4-ylmethyl)-thiazole-4-carboxylic acid ethyl ester (3.745 g, 8.28 mmol) in EtOH (100 mL) and THF (40 mL) with 5 M LiOH (8.3 mL, 41.4 mmol) and stir at room temperature for 18 h. Add 5 N HCl (9 mL) bringing pH to 2. Concentrate the reaction mixture by rotavap, extract into EtOAc (3×330 mL), dry organics (MgSO$_4$), filter, and concentrate to give 3.86 g (>100%) of 5-((S)-7-cyano-2-isopropoxycarbonylamino-2,3-dihydro-1H-cyclopenta[b]indol-4-ylmethyl)-thiazole-4-carboxylic acid as a pale yellow solid. LC-ES/MS m/z 425 (M+1), 423 (M–H), T$_R$=2.3 min.

Prepare the following compound essentially as described for Intermediate 62.

| | | | MS m/z |
|---|---|---|---|
| Intermediate 63 | (R)-5-{2-[(dimethylamino)-sulfonyl]-amino-7-cyano-2,3-dihdro-1H-cyclopenta[b]indol-4-ylmethyl}-thiazole-4-carboxylic acid | | 446 (M + 1) |

Intermediate 64

{(S)-7-Cyano-4-[4-(2-trimethylsilanyl-ethoxycarbonylamino)-thiazol-5-ylmethyl]-1,2,3,4-tetrahydro-cyclopenta[b]indol-2-yl}-carbamic acid isopropyl ester

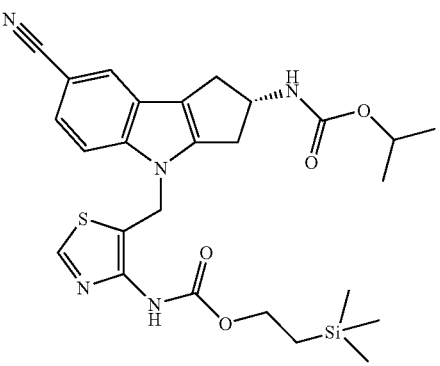

Slowly add diphenylphosphorylazide (5.45 g, 4.27 mL, 19.8 mmol) to a refluxing mixture of 5-((S)-7-cyano-2-isopropoxycarbonylamino-2,3-dihydro-1H-cyclopenta[b]indol-4-ylmethyl)-thiazole-4-carboxylic acid (3.82 g, 9.00 mmol), Et$_3$N (2.00 g, 2.76 mL, 19.8 mmol), and 2-(trimethylsilyl)-ethanol (10 mL, 8.25 g, 69.8 mmol) in toluene (270 mL). Continue at reflux for 3 h, then cool to room temperature. Concentrate the reaction mixture to give 14.85 g crude.

Purify on silica gel (115 g) using 20-60% EtOAc/hexanes to give 4.06 g (84%) of the product as a yellow solid. LC-ES/MS m/z 562 (M+Na), 538 (M−H), $T_R$=3.1 min.

Prepare the following compound essentially as described for Intermediate 64.

| Intermediate 65 | (R)-{5-[2-(dimethylamino)sulfonyl-amino-7-cyano-2,3-dihdro-1H-cyclopenta[b]indol-4-ylmethyl]-thiazol-4-yl}-carbamic acid-2-trimethylsilanyl-ethyl ester | MS m/z 559 (M − 1) |
|---|---|---|

Example 91

[(S)-4-(4-Amino-thiazol-5-ylmethyl)-7-cyano-1,2,3,4-tetrahydro-cyclopenta[b]indol-2-yl]-carbamic acid isopropyl ester

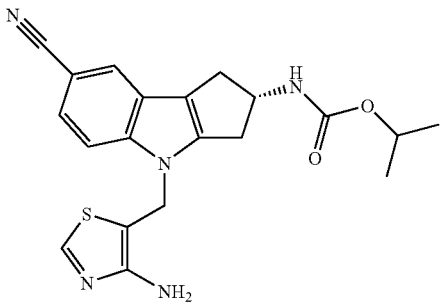

Treat a mixture of {(S)-7-cyano-4-[4-(2-trimethylsilanyl-ethoxycarbonylamino)-thiazol-5-ylmethyl]-1,2,3,4-tetrahydro-cyclopenta[b]indol-2-yl}-carbamic acid isopropyl ester (3.98 g, 7.37 mmol) in THF (40 mL) with tetrabutylammonium fluoride (1.0 M in THF, 14.74 mL, 14.74 mmol) and heat to 50° C. Cool to room temperature after 40 min, dilute with water (40 mL), and evaporate the THF under vacuum. Filter a solid off of the resulting aqueous slurry and dry in vacuo at 40° C. to give 2.43 g product as a tan solid. Dissolve the product in 250 mL boiling EtOAc, then concentrate to a volume of about 100 mL. Add 50 mL hexanes, then cool the mixture to −26° C. in a freezer overnight. Collect the solid and dry in vacuo at 40° C. to give 1.74 g (60%) of the product as a brown solid. LC-ES/MS 396 (M+1), $T_R$=2.2 min.

Example 92

(R)—N'-[4-(4-amino-thiazol-5-ylmethyl)-7-cyano-1,2,3,4-tetrahydro-cyclopenta[b]indol-2-yl]-N,N-dimethylsulfamide

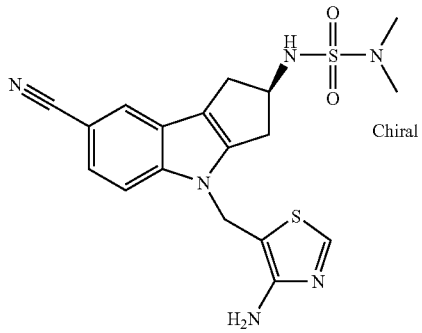

Prepare the titled compound essentially as described for Example 91, using (R)-{5-[2-(dimethylamino)sulfonyl-amino-7-cyano-2,3-dihydro-1H-cyclopenta[b]indol-4-ylm-ethyl]-thiazol-4-yl}-carbamic acid-2-trimethylsilanyl-ethyl ester and heating the reaction at 60° C. for 3 hours. After cooling to room temperature dilute the reaction with ethyl acetate (200 mL) and wash with water and brine. Dry the organic portion over sodium sulfate, filter, and concentrate. Purify by silica gel chromatography (100% EtOAc to 5% MeOH/EtOAc) to obtain 0.94 g (60%). LCMS 417.0 (M+1).

Intermediate 66

(S)-(7-Formyl-4-pyridin-2-ylmethyl-1,2,3,4-tetrahydro-cyclopenta[b]indol-2-yl)-carbamic acid isopropyl ester Dissolve (S)-(7-cyano-4-pyridin-2-ylmethyl-1,2,3,4-tetrahydro-cyclopenta[b]indol-2-yl)-carbamic acid isopropyl ester (200 mg, 0.53 mmol) in 88% formic acid (10 ml) and water (1 mL). Add aluminum-nickel catalyst (50/50 wt %) and heat at 90° C. for 24 h. Add water (1 mL) and heat for an additional 24 h. After cooling to room temperature, add methanol and filter off the catalyst through Celite®. Dilute with ethyl acetate and basify to pH=10 using 10% potassium carbonate. Separate the phases and wash the organic phase with 10% potassium carbonate. Dry the organic portion over anhydrous sodium sulfate, filter, and concentrate to obtain the title compound as an orange oil (181 mg, 91%). Use the crude product without further manipulation. MS (m/z): 378.2 (M+1).

Example 93

(S)-[7-(Methoxyimino-methyl)-4-pyridin-2-ylmethyl-1,2,3,4-tetrahydro-cyclopenta[b]indol-2-yl]-carbamic acid isopropyl ester

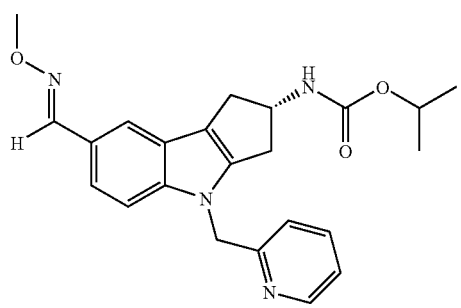

Dissolve (S)-(7-formyl-4-pyridin-2-ylmethyl-1,2,3,4-tetrahydro-cyclopenta[b]indol-2-yl)-carbamic acid isopropyl ester (181 mg, 0.48 mmol) in methanol (10 mL) and 1.0 N sodium hydroxide (2.4 ml, 2.4 mmol). Add methoxyamine hydrochloride (120 mg, 1.44 mmol) and stir at room temperature overnight. Dilute with ethyl acetate, wash with 10% potassium carbonate, dry over anhydrous sodium sulfate, filter, and concentrate. Purify the crude product on a 12 g silica gel column eluting with 30% ethyl acetate/dichloromethane to obtain the pure title compound (53 mg, 27%). LCMS 407.1 (M+1).

Prepare the oximes, Examples 94-101, in Table 6, essentially according to the procedures described for Intermediate 66 and Example 93, starting with the appropriate nitrile.

TABLE 6

| Example | Chemical Name | MS m/z |
|---|---|---|
| 94 | (S)-[7-(Methoxyimino-methyl)-4-pyridin-2-ylmethyl-1,2,3,4-tetrahydro-cyclopenta[b]indol-2-yl]-carbamic acid ethyl ester | 393 (M + 1) |
| 95 | (S)-[4-Isothiazol-3-ylmethyl-7-(methoxyimino-methyl)-1,2,3,4-tetrahydro-cyclopenta[b]indol-2-yl]-carbamic acid isopropyl ester | 413 (M + 1) |
| 96 | (S)-[4-Isothiazol-3-ylmethyl-7-(methoxyimino-methyl)-1,2,3,4-tetrahydro-cyclopenta[b]indol-2-yl]-carbamic acid ethyl ester | 399 (M + 1) |
| 97 | (R)-N'-[4-Isothiazol-3-ylmethyl-7-(methoxyimino-methyl)-1,2,3,4-tetrahydro-cyclopenta[b]indol-2-yl]-N,N-dimethylsulfamide | 434 (M + 1) |
| 98 | (R)-N'-[7-(Methoxyimino-methyl)-4-thiazol-2-ylmethyl-1,2,3,4-tetrahydro-cyclopenta[b]-indol-2-yl]-N,N-dimethylsulfamide | 434 (M + 1) |
| 99 | (R)-N'-[4-(6-Fluoro-pyridin-2-ylmethyl)-7-(methoxyimino-methyl)-1,2,3,4-tetrahydro-cyclopenta[b]indol-2-yl]-N,N-dimethylsulfamide | 446 (M + 1) |
| 100 | (R)-N'-[7-(Methoxyimino-methyl)-4-pyrazin-2-ylmethyl-1,2,3,4-tetrahydro-cyclopenta[b]-indol-2-yl]-N,N-dimethylsulfamide | 429 (M + 1) |
| 101 | (R)-N'-[7-(Methoxyimino-methyl)-4-pyridin-2-ylmethyl-1,2,3,4-tetrahydro-cyclopenta[b]-indol-2-yl]-N,N-dimethylsulfamide | 428 (M + 1)<br>426 (M − 1) |

Example 102

(±)-[4-(3-Amino-pyrazin-2-ylmethyl)-7-cyano-1,2,3,4-tetrahydro-cyclopenta[b]indol-2-yl]-carbamic acid isopropyl ester In a screw-cap vial, dissolve (±)-[4-(3-chloro-pyrazin-2-ylmethyl)-7-cyano-1,2,3,4-tetrahydro-cyclopenta[b]indol-2-yl]-carbamic acid isopropyl ester (30 mL, 0.073 mmol) in 1-methyl-2-pyrrolidinone (NMP) (0.5 mL) and cool to −78° C. Condense NH₃ into the reaction mixture (1 mL), seal the reaction vessel, and warm to room temperature over 24 h. Heat the reaction up to 50° C. for 18 h, then at 80° C. for 72 h. Cool the reaction in a dry ice bath. Carefully open the reaction vessel and allow the liquid NH₃ to evaporate. Dissolve the residue in EtOAc (50 mL) and wash the organics with water (3×20 mL). Dry the organics (MgSO₄), filter, and concentrate to give 27 mg crude product as a colorless film. Purify on 4 g silica gel [50-100% EtOAc/(1:1 CH₂Cl₂/hexanes)] to give 8 mg (28%) of the title compound as a colorless film. LCMS 100% @ 4.23 min m/z 391 (M+H), 389 (M−H).

Example 103

(S)-[4-(3-Amino-pyrazin-2-ylmethyl)-7-cyano-1,2,3,4-tetrahydro-cyclopenta[b]indol-2-yl]-carbamic acid isopropyl ester

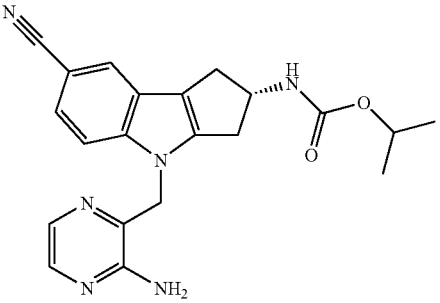

Dissolve (S)-[4-(3-chloro-pyrazin-2-ylmethyl)-7-cyano-1,2,3,4-tetrahydro-cyclopenta[b]indol-2-yl]-carbamic acid isopropyl ester (8.89 g, 21.7 mmol) in NMP (36 mL) and distribute the mixture evenly between three 10-20 mL microwave reactor vials. Cool each reaction vessel to 0° C. and sparge with anhydrous NH₃ for 15 min. Seal each vessel and heat to 200° C. for 1 h in a microwave reactor. Combine the reaction mixtures together in water (500 mL) and sonicate for 20 min. Filter off a tan solid, then dissolve the solid in EtOAc (500 mL). Dry the organics (MgSO₄), filter, and concentrate to a volume of 10 mL. Dilute the organics with MeOH (20 mL) and CH₂Cl₂ (10 mL) and absorb onto silica gel in vacuo. Purify on silica gel (340 g) using 1-10% (2 M NH₃/MeOH)/(1:1 CH₂Cl₂/hexanes) to afford 1.50 g (18%) of the title compound as a yellow solid. MS (m/z) 391 (M+1), 389 (M−1). Pool and concentrate fractions containing impure product (1.2 g), and re-purify on silica gel (80 g) using 3-8% (2 M NH₃/MeOH)/(1:1 CH₂Cl₂/hexanes) to afford a second crop (503 mg, 6%) of the title compound as a yellow solid.

Example 104

[3-((S)-7-Cyano-2-isopropoxycarbonylamino-2,3-dihydro-1H-cyclopenta[b]indol-4-ylmethyl)-pyridin-2-ylamino]-acetic acid

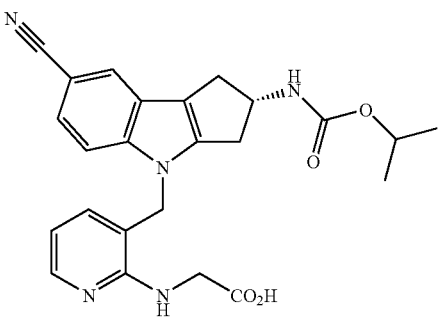

Dissolve [(S)-4-(2-amino-pyridin-3-ylmethyl)-7-cyano-1,2,3,4-tetrahydro-cyclopenta[b]indol-2-yl]-carbamic acid isopropyl ester (253 mg, 0.650 mmol) in EtOH (25 mL). Add 3 Å molecular sieves and glyoxylic acid monohydrate (239 mg, 2.60 mmol), then stir at 40-110° C. for 18 h under hydrogen (60 psi, 4.08 bar). Filter the reaction through a pad of diatomaceous earth and wash the catalyst/sieves with THF (50 mL). Combine the filtrate and concentrate in vacuo to a yellow oil. Triturate with water (30 mL) and sonicate the resulting aqueous slurry for 5 min. Filter off a tan solid and dry in vacuo. Triturate the solid with $Et_2O$ (5 mL) and sonicate the slurry for 30 min. Filter to obtain 190 mg (65%) of the product as a tan solid. LCMS 100% @ 3.99 min m/z 448 (M+H), 446 (M−H).

We claim:

1. A compound of Formula (I):

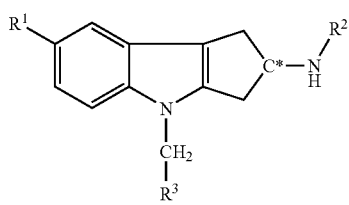

Formula (I)

wherein, the "C*" carbon center may be in the R, S or R/S configuration;

$R^1$ represents cyano, —CH=NOCH$_3$, —OCHF$_2$, or —OCF$_3$;

$R^2$ represents —COR$^{2a}$ or —SO$_2$R$^{2b}$;

$R^{2a}$ represents ($C_1$-$C_4$)alkyl, ($C_1$-$C_4$)alkoxy, cyclopropyl, or —NR$^a$R$^b$;

$R^{2b}$ represents ($C_1$-$C_4$)alkyl, cyclopropyl, or —NR$^a$R$^b$;

$R^a$ and $R^b$ each independently represent at each occurrence H or ($C_1$-$C_4$)alkyl; and $R^3$ represents a heteroaryl group selected from the group consisting of pyridinyl, pyrimidinyl, pyrazinyl, pyridazinyl, thiazolyl, isothiazolyl, and thiadiazolyl, each of which is optionally substituted with 1 or 2 substituents independently selected from the group consisting of methyl, ethyl, bromo, chloro, fluoro, —CHF$_2$, —CF$_3$, hydroxy, amino, and —NHCH$_2$CO$_2$H;

or a pharmaceutically acceptable salt thereof.

2. The compound or salt according to claim 1 wherein $R^1$ represents cyano, or —CH=NOCH$_3$.

3. The compound or salt according to claim 2 wherein $R^1$ represents cyano.

4. The compound or salt according to claim 1 wherein $R^{2a}$ represents ($C_1$-$C_4$)alkyl, ($C_1$-$C_4$)alkoxy, cyclopropyl, or N(CH$_3$)$_2$ and $R^{2b}$ represents ($C_1$-$C_4$)alkyl, cyclopropyl, —N(CH$_3$)$_2$ or —N(C$_2$H$_5$)$_2$.

5. The compound or salt according to claim 4 wherein $R^2$ represents —COR$^{2a}$ and $R^{2a}$ represents ethyl, isopropyl, methoxy, ethoxy, propoxy, isopropoxy, isobutoxy, tert-butoxy, cyclopropyl, or —N(CH$_3$)$_2$.

6. The compound or salt according to claim 5 wherein $R^{2a}$ represents isopropoxy.

7. The compound or salt according to claim 4 wherein $R^2$ represents SO$_2$R$^{2b}$ and $R^{2b}$ represents methyl, ethyl, propyl, cyclopropyl, —N(CH$_3$)$_2$ or —N(C$_2$H$_5$)$_2$.

8. The compound or salt according to claim 7 wherein $R^{2b}$ represents —N(CH$_3$)$_2$.

9. The compound or salt according to claim 1 wherein $R^2$ represents —$COR^{2a}$ and the "C*" carbon center is in the S configuration.

10. The compound or salt according to claim 1 wherein $R^2$ represents —$SO_2R^{2b}$ and the "C*" carbon center is in the R configuration.

11. The compound or salt according to claim 1 wherein $R^3$ represents a heteroaryl group selected from the group consisting of pyridinyl, pyrimidinyl, pyrazinyl, pyridazinyl, thiazolyl, isothiazolyl, and thiadiazolyl, each of which is optionally substituted with 1 or 2 substituents independently selected from the group consisting of methyl, bromo, chloro, fluoro, $CHF_2$, hydroxy, amino, and —$NHCH_2CO_2H$.

12. The compound or salt according to claim 11 wherein $R^3$ represents 6-fluoro-pyridin-2-yl, pyridin-2-yl, 3-hydroxy-pyridin-2-yl, 6-difluoromethyl-pyridin-2-yl, 2-amino-pyridin-3-yl, 2-carboxymethylamino-pyridin-3-yl, thiazol-4-yl, 2-methyl-thiazol-4-yl, 2-chloro-thiazol-4-yl, thiazol-2-yl, thiazol-5-yl, 4-amino-thiazol-5-yl, pyrazin-2-yl, 5-methyl-pyrazin-2-yl, 3-chloro-pyrazin-2-yl, 6-methyl-pyrazin-2-yl, 3-amino-pyrazin-2-yl, or 3-methyl-pyrazin-2-yl.

13. The compound or salt according to claim 12 wherein $R^3$ represents pyridin-2-yl, 2-amino-pyridin-3-yl, thiazol-5-yl, or 4-amino-thiazol-5-yl.

14. The compound or salt according to claim 1 wherein, the "C*" carbon center is in the S configuration when $R^2$ represents —$COR^{2a}$ and in the R configuration when $R^2$ represents —$SO_2R^{2b}$;

$R^1$ represents cyano or —$CH=NOCH_3$;

$R^{2a}$ represents ethyl, isopropyl, methoxy, ethoxy, propoxy, isopropoxy, isobutoxy, tert-butoxy, cyclopropyl, or $N(CH_3)_2$; and $R^{2b}$ represents methyl, ethyl, propyl, cyclopropyl, —$N(CH_3)_2$ or —$N(C_2H_5)_2$; and $R^3$ represents 6-fluoro-pyridin-2-yl, pyridin-2-yl, 3-hydroxy-pyridin-2-yl, 6-difluoromethyl-pyridin-2-yl, 2-amino-pyridin-3-yl, 2-carboxymethylamino-pyridin-3-yl, pyrimidin-4-yl, pyrimidin-2-yl, 2-chloro-pyrimidin-4-yl, thiazol-4-yl, 2-methyl-thiazol-4-yl, 2-chloro-thiazol-4-yl, thiazol-2-yl, thiazol-5-yl, 4-amino-thiazol-5-yl, pyrazin-2-yl, 5-methyl-pyrazin-2-yl, 3-chloro-pyrazin-2-yl, 6-methyl-pyrazin-2-yl, 3-amino-pyrazin-2-yl, 3-methyl-pyrazin-2-yl, pyridazin-3-yl, 5-bromo-isothiazol-3-yl, isothiazol-3-yl, 4,5-dichloro-isothiazol-3-yl, or [1,2,5]thiadiazol-3-yl.

15. A compound selected from the group consisting of (S)-(7-cyano-4-pyridin-2-ylmethyl-1,2,3,4-tetrahydro-cyclopenta[b]indol-2-yl)-carbamic acid isopropyl ester; (S)-(7-cyano-4-thiazol-5-ylmethyl-1,2,3,4-tetrahydro-cyclopenta[b]indol-2-yl)-carbamic acid isopropyl ester; (S)-[4-(2-amino-pyridin-3-ylmethyl)-7-cyano-1,2,3,4-tetrahydro-cyclopenta[b]indol-2-yl]-carbamic acid isopropyl ester; (R)—N'-[4-(4-amino-thiazol-5-ylmethyl)-7-cyano-1,2,3,4-tetrahydro-cyclopenta[b]indol-2-yl]-N,N-dimethylsulfamide; and (S)-[4-(4-amino-thiazol-5-ylmethyl)-7-cyano-1,2,3,4-tetrahydro-cyclopenta[b]indol-2-yl]-carbamic acid isopropyl ester, or a pharmaceutically acceptable salt thereof.

16. A method of treating hypogonadism, reduced bone mass or density, osteoporosis, osteopenia, reduced muscle mass or strength, sarcopenia, Age Related Functional Decline, delayed puberty in boys, anemia, male or female sexual dysfunction, erectile dysfunction, reduced libido, depression, or lethargy, comprising administering to a patient in need thereof a compound or salt according to claim 1.

17. The method according to claim 16 for treating reduced bone mass or density, osteoporosis, osteopenia, or reduced muscle mass or strength.

18. A pharmaceutical composition comprising a compound or salt according to claim 1 in combination with one or more pharmaceutically acceptable carriers, diluents, or excipients.

19. The compound according to claim 15 which is (S)-(7-cyano-4-pyridin-2-ylmethyl-1,2,3,4-tetrahydro-cyclopenta[b]indol-2-yl)-carbamic acid isopropyl ester.

20. The pharmaceutical composition according to claim 18 comprising the compound which is (S)-(7-cyano-4-pyridin-2-ylmethyl-1,2,3,4-tetrahydro-cyclopenta[b]indol-2-yl)-carbamic acid isopropyl ester.

* * * * *

```
                            SEQUENCE LISTING

<160> NUMBER OF SEQ ID NOS: 3

<210> SEQ ID NO 1
<211> LENGTH: 15
<212> TYPE: DNA
<213> ORGANISM: Artificial
<220> FEATURE:
<223> OTHER INFORMATION: Synthetic Construct

<400> SEQUENCE: 1
ggttcttgga gtact                                                      15

<210> SEQ ID NO 2
<211> LENGTH: 15
<212> TYPE: DNA
<213> ORGANISM: Artificial
<220> FEATURE:
<223> OTHER INFORMATION: Synthetic Construct

<400> SEQUENCE: 2
tgtacaggat gttct                                                      15

<210> SEQ ID NO 3
<211> LENGTH: 15
<212> TYPE: DNA
<213> ORGANISM: Artificial
<220> FEATURE:
<223> OTHER INFORMATION: Synthetic Construct

<400> SEQUENCE: 3
tgtacaggat gttct                                                      15
```